United States Patent [19]

Band

[11] Patent Number: 5,843,694
[45] Date of Patent: Dec. 1, 1998

[54] METHODS FOR IDENTIFICATION OF MODULATORY COMPOUNDS FOR THE EXPRESSION OF THE NES1 PROTEIN

[75] Inventor: Vimla Band, Natick, Mass.

[73] Assignee: New England Medical Center Hospitals, Inc., Boston, Mass.

[21] Appl. No.: 628,198

[22] Filed: Apr. 5, 1996

Related U.S. Application Data

[62] Division of Ser. No. 467,155, Jun. 6, 1995.

[51] Int. Cl.$^6$ .......................................................... F41G 3/26
[52] U.S. Cl. ............................ 435/23; 435/212; 435/219; 435/226
[58] Field of Search .............................. 435/6, 7.1, 320.1, 435/212, 219, 23, 24, 213, 226; 536/23.5, 24.31; 530/350

[56] References Cited

U.S. PATENT DOCUMENTS 5,470,970   11/1995   Sagar et al. ............................ 536/23.5

OTHER PUBLICATIONS

Lee et al. (1992a) "Down–regulation of a member of the S100 gene family in mammary carcinoma cells and reexpression by azadeoxycytidine" Proc. Natl. Acad. Sci. USA, 89, 2504–2908. See page 2506, right column paragraph 2 to the end of the result section, Mar. 1992.
Lee et al. (1992b) "Transcriptional downregulation of gap–junction protein blocks junctional communication in human mammary tumor cell lines" J. Cell Biol. 118, 1213–1221. See page 1218, right column, paragraph 2 to the end of the result section on page, Sep. 1992.
Aznavoorian et al., Cancer 71:1368–1383 (1993).
Baker et al., Science 249:912–915 (1990).
Band et al., Cancer Res. 50:7351–7357 (1990).
Band et al., J. Cell Physiol. 138:106–114 (1989).
Basset et al., Nature 348:699–704 (1990).
Blasi, BioEssays 15:105–111 (1993).
Boice et al., New Eng. J. Med. 326:781–785 (1992).
Boice et al., Radiat. Res. 125:214–222 (1991).
Boothman et al., Rad. Res. 138:s68–s71 (1994).
Borek and Sachs, Nature 210:276–278 (1966).
Borek, Nature 283:776–778 (1980).
Bosmann et al., Nature 261:499–501 (1976).
Brenner, Nature 334:528–530 (1988).
Cheah et al., J. Biol. Chem. 265:7180–7187 (1990).
Cronkite et al., Rad. Res. 138:266–271 (1994).
Farber, Cancer Res. 44:4217–4223 (1984).
Fornace, Annu. Rev. Genet. 26:507–526 (1992).
Gasic et al., Proc. Natl. Acad. Sci. USA 89:2317–2320 (1992).
Gudas et al., Cell Growth & Diff. 5:295–304 (1994).

Huang et al., Science 242:1563–1566 (1988).
Kastan et al., Cancer Res. 51:6304–6311 (1991).
Keyomarsi et al., Cancer Res. 51:3602–3609 (1991).
Kook et al., EMBO J. 13:3983–3991 (1994).
Liotta, Sci. Amer. 54–63 (1992).
Liotta and Stetler–Stevenson, Cancer Res. 51:5054–5059 (1991).
Manfioletti et al., Mol. Cell Biol. 13:4976–4985 (1993).
Melino et al., Mol. Cell Biol. 14:6584–6596 (1994).
Namba et al., Int. J. Cancer 35:275–280 (1985).
Norbury and Nurse, Annu. Rev. Biochem. 61:441–470 (1992).
Orita et al., Proc. Natl. Acad. Sci. USA 86:2766–2770 (1989).
Price et al., Cancer Res. 50:717–721 (1990).
Ringe, Curr. Biol. 2:545–547 (1992).
Sheffield et al., Proc. Natl. Acad. Sci. USA 86:232–236 (1989).
Sherwood et al., Proc. Natl. Acad. USA 90:3353–3357 (1993).
Smyth et al., J. Biol. Chem. 267:24418–24425 (1992).
Spyratos et al., J. Natl. Cancer Inst. 84:1266–1272 (1992).
Stetler–Stevenson et al., FASEB J. 7:1434–1441 (1993).
Terzaghi and Little, Cancer Res. 36:1367–1374 (1976).
Thraves et al., Proc. Natl. Acad. Sci. USA 87:1174–1177 (1990).
Tokunaga et al., Rad. Res. 138:209–223 (1994).
Torres–Rosado et al., Proc. Natl. Acad. Sci. USA 90:7181–7185 (1993).
Tuynder et al., Proc. Natl. Acad. Sci. USA 88:2638–2642 (1991).
Wazer et al., Mol. Cell. Biol. 14:2468–2478 (1994).
Winstanly et al., Br. J. Cancer 767–772 (1992).
Wu and Levine, Proc. Natl. Acad. Sci. USA 91:3602–3606 (1994).
Xu et al., Cell 78:473–485 (1994).
Yang et al., Int. J. Radiat. Biol. 56:605–609 (1989).
Yaswen et al., Proc. Natl. Acad. Sci. USA 87:7360–7364 (1990).
Liu et al., Cancer Research 56:3371–3379, 1996.
Sager et al., Cold Spring Harbor Symposia on Quantitative Biology, vol. LIX, pp. 537–546, 1994.
Zou et al., Science 263:526–529, 1994.

*Primary Examiner*—Robert A. Wax
*Assistant Examiner*—Nashaat T. Nashed
*Attorney, Agent, or Firm*—Fish & Richardson, P.C.

[57] ABSTRACT

The expression and purification of normal epithelial specific polypeptide (NES 1) which is expressed in normal cells, but not in radiation transformed cells, are described. Both the DNA sequence encoding the NES1 and the corresponding amino acid sequence are disclosed. Also, disclosed are methods for carcinoma detection and treatment using the NES1 as well as methods of identifying compounds modulating the expression and activity of NES1.

5 Claims, 7 Drawing Sheets

Comparison of Sequences near putative active site

|  | 86 | 137 | 223 | 224 | 227 | 228 | 229 | 230 | 231 | 241 | 243 | 245 |
|---|---|---|---|---|---|---|---|---|---|---|---|---|
| NES 1 | H | D | D | P | S | D | S | G | G | G | L | W |
| Human Pancreatic Trypsinogen III | H | D | D | S | R | D | S | G | G | G | V | W |
|  | ▲ | ▲ | △ | △ |  | ▲ |  |  |  | △ | △ | △ |

▲: Catalytic triad

△: Residues important for substrate binding and specificity

FIG. 9A

Alignment of NES 1 amino acid sequence with other serine proteases

```
               1                                                      50
Mmtryar   ..MSALLILA LVGA......  ..........  AVAFPVDD.D DKIVG...GY
Hstryivb  .....LELHP LLGGRTWRAA  RDADGCEALG  TVAVPFDD.D DKIVG...GY
Rntrypvb  ..MKICIFFT LLGT......  ..........  VAAFPTEDND DRIVG...GY
Sstrypii  .......... ..........  ..........  .AAFATE..D DKIVG...GY
Nes1      MRAPHLHLSA ASGARALAKL  LPLLMAQLWA  AEAALLPQND TRLDPEAYGA 51                                                    100
Mmtryar   TCRESSVPYQ VSLNAGYHF.  CGGSLINDQW  VVSAAHCYKY RIQVRLGEHN
Hstryivb  TC.ENSLPYQ VSLNSGSHF.  CGGSLISEQW  VVSAAHCYKT RIQVRLGEHN
Rntrypvb  TCQEHSVPYQ VSLNAGSHI.  CGGSLITDQW  VLSAAHCYHP QLQVRLGEHN
Sstrypii  ECKAYSQPHQ VSLNSGYHF.  CGGSLVNENW  VVSAAHCYQS RVEVRLGEHN
Nes1      PCARGSQPWQ VSLFNGLSFH  CAGVLVDQSW  VLTAAHCGNK PLWARVGDDH
                                                 ▲
               101                                                   150
Mmtryar   INVLEGNEQF VDSAKIIRHP  NYN.......  .SWTLDNDIM LIKLASPVTL
Hstryivb  IKVLEGNEQF INAAKIIRHP  KYN.......  .RDTLDNDIM LIKLSSPAVI
Rntrypvb  IYEIEGAEQF IDAAKMILHP  DYD.......  .KWTVDNDIM LIKLKSPATL
Sstrypii  IQVTEGSEQF ISSSRVIRHP  NYS.......  .SYNIDNDIM LIKLSKPATL
Nes1      LLLLQG.EQL RRTTRSVVHP  KYHQGSGPIL  PRRTDEHDLM LLKLARPVVP
                                EXTRA INSERT         ▲
               151                                                   200
Mmtryar   NARVASVPLP SSCAPAGTQC  LISGWGNTLS  NGVNNPDLLQ CVDAPVLPQA
Hstryivb  NARVSTISLP TAPPAAGTEC  LISGWGNTLS  FGADYPDELK CLDAPVLTQA
Rntrypvb  NSKVSTIPLP QYCPTAGTEC  LVSGWG.VLK  FGFESPSVLQ CLDAPVLSDS
Sstrypii  NTYVQPVALP TSCAPAGTMC  TVSGWGNTMS  STAD.KNKLQ CLNIPILSYS
Nes1      GPRVRALQLP YRCAQPGDQC  QVAGWGTTAA  RRVKYNKGLT CSSITILSPK 201                                                   250
Mmtryar   DCEASYPGDI TNNMICVGFL  EGGKDSCQGD  SGGPVVCNGE LQGIVSWG.Y
Hstryivb  ECKASYPGKI TNSMFCVGFL  EGGKDSCQRD  SGGPVVCNGQ LQGVVSWG.H
Rntrypvb  VCHKAYPRQI TNNMFCLGFL  EGGKDSCQYD  SGGPVVCNGE VQGIVSWG.D
Sstrypii  DCNNSYPGMI TNAMFCAGYL  EGGKDSCQGD  SGGPVVCNGE LQGVVSWG.Y
Nes1      ECEVFYPGVV TNNMICAG.L  DRGQDPCQSD  SGGPLVCDET LQGILSWGVY
                                    △△              ▲   △△△
               251           280
Mmtryar   GCAQPDAPGV YTKVCNYVDW  IQNTIADN*.
Hstryivb  GCAWKNRPGV YTKVYNYVDW  IKDTIAANS*
Rntrypvb  GCALEGKPGV YTKVCNYLNW  IQQTVAAN*.
Sstrypii  GCAEPGNPGV YAKVCIFNDW  LTSTMATY*.
Nes1      PCGSAQHPAV YTQICKYMSW  INKVIRSN*.
```

FIG. 9B

```
  1  MRAPHLHLSA ASGARALAKL LPLLMAQLWA AEAALLPQND TRLDPEAYGA
 51  PCARGSQPWQ VSLFNGLSFH CAGVLVDQSW VLTAAHCGNK PLWARVGDDH
101  LLLQGEQLR  RTTRSVVHPK YHQGSGPILP RRTDEHDLML LKLARPVVPG
151  PRVRALQLPY RCAQPGDQCQ VAGWGTTAAR RVKYNKGLTC SSITILSPKE
201  CEVFYPGVVT NNMICAGLDR GQDPCQSDSG GPLVCDETLQ GILSWGVYPC
251  GSAQHPAVYT QICKYMSWIN KVIRSN* (SEQ ID NO: 1)
```

FIG. 10

```
   1  ACCAGCGGCA GACCACAGGC AGGGCAGAGG CACGTCTGGG TCCCCTCCCT
  51  CCTTCCTATC GGCGACTCCC AGATCCTGGC CATGAGAGCT CCGCACCTCC
 101  ACCTCTCCGC CGCCTCTGGC GCCCGGGCTC TGGCGAAGCT GCTGCCGCTG
 151  CTGATGGCGC AACTCTGGGC CGCAGAGGCG GCGCTGCTCC CCCAAAACGA
 201  CACGCGCTTG GACCCCGAAG CCTATGGCGC CCCGTGCGCG CGCGGCTCGC
 251  AGCCCTGGCA GGTCTCGCTC TTCAACGGCC TCTCGTTCCA CTGCGCGGGT
 301  GTCCTGGTGG ACCAGAGTTG GGTGCTGACG GCCGCGCACT GCGGAAACAA
 351  GCCACTGTGG GCTCGAGTAG GGGATGATCA CCTGCTGCTT CTTCAGGGCG
 401  AGCAGCTCCG CCGGACGACT CGCTCTGTTG TCCATCCCAA GTACCACCAG
 451  GGCTCAGGCC CCATCCTGCC AAGGCGAACG GATGAGCACG ATCTCATGTT
 501  GCTAAAGCTG GCCAGGCCCG TAGTGCCGGG GCCCCGCGTC CGGGCCCTGC
 551  AGCTTCCCTA CCGCTGTGCT CAGCCCGGAG ACCAGTGCCA GGTTGCTGGC
 601  TGGGGCACCA CGGCCGCCCG GAGAGTGAAG TACAACAAGG GCCTGACCTG
 651  CTCCAGCATC ACTATCCTGA GCCCTAAAGA GTGTGAGGTC TTCTACCCTG
 701  GCGTGGTCAC CAACAACATG ATATGTGCTG GACTGGACCG GGGCCAGGAC
 751  CCTTGCCAGA GTGACTCTGG AGGCCCCCTG GTCTGTGACG AGACCCTCCA
 801  AGGCATCCTC TCGTGGGGTG TTTACCCCTG TGGCTCTGCC CAGCATCCAG
 851  CTGTCTACAC CCAGATCTGC AAATACATGT CCTGGATCAA TAAAGTCATA
 901  CGCTCCAACT GATCCAGATG CTACGCTCCA GCTGATCCAG ATGTTATGCT
 951  CCTGCTGATC CAGATGCCCA GAGGCTCCAT CGTCCATCCT CTTCCTCCCC
1001  AGTCGGCTGA ACTCTCCCCT TGTCTGCACT GTTCAAACCT CTGCCGCCCT
1051  CCACACCTCT AAACATCTCC CCTCTCACCT CATTCCCCCA CCTATCCCCA
1101  TTCTCTGCCT GTACTGAAGC TGAAATGCAG GAAGTGGTGG CAAAGGTTTA
1151  TTCCAGAGAA GCCAGGAAGC CGGTCATCAC CCAGCCTCTG AGAGCAGTTA
1201  CTGGGGTCAC CCAACCTGAC TTCCTCTGCC ACTCCCCGCT GTGTGACTTT
1251  GGGCAAGCCA AGTGCCCTCT CTGAACCTCA GTTTCCTCAT CTGCAAAATG
1301  GGAACAATGA CGTGCCTACC TCTTAGACAT GTTGTGAGGA GACTATGATA
1351  TAACATGTGT ATGTAAATCT TCATGTGATT GTCATGTAAG CTTAACACA
1401  GTGGGTGGTG AGTTCTGACT AAAGGTTACC TGTTGTCGTG AAAAAAAAA
1451  AAAA  (SEQ ID NO: 2)
```

METHODS FOR IDENTIFICATION OF MODULATORY COMPOUNDS FOR THE EXPRESSION OF THE NES1 PROTEIN

This is divisional of copending application Ser. No. 08/467,155, filed Jun. 6, 1995

BACKGROUND OF THE INVENTION

This invention relates to cancer diagnostics and therapeutics.

Carcinomas, the malignant tumors arising from epithelial cells, constitute the majority of human cancers. In nearly all cases, the precise etiology of epithelial cancers is unknown, but multiple etiological agents, including radiation, viruses, carcinogens, and dietary factors (Farber, Cancer Res. 44:4217–4223, 1984), are thought to alter common cellular pathways resulting in uncontrolled growth, a hallmark of the tumorigenic process.

The carcinogenic potential of radiation in humans was realized within the first decade after the discovery of X-rays by Roentgen in 1895 (Hall, *Radiobiology for the Radiologist*, 3d ed., J. B. Lippincott, Philadelphia, 1988) and this was confirmed in later years through epidemiologic studies of the survivors of atomic bombing of Hiroshima and Nagasaki (Tokunaga et al., Rad. Res. 138:209–223, 1994). These data provided evidence that various forms of neoplasia, including breast cancer, represent a significant late effect in human populations exposed to ionizing radiation. Strong evidence for the role of fractionated radiation in breast cancer was also provided by studies on women who received radiation for treatment of breast cancer or pulmonary tuberculosis (Boice et al., New Eng. J. Med. 326:781–785, 1992; Boice et al., Radiat. Res. 125:214–222, 1991). As a result of these types of studies, the Bier Committees ranked female breast tissue as having a high relative sensitivity to radiation-induced oncogenesis (Beir, Report In: Health Effects of Exposure to Low Levels of Ionizing Radiation. National Research Council, pp. 1–421, 1990).

Currently, breast carcinomas are one of the leading causes of cancer-related deaths of women in North America and Europe. About 180,000 new cases of breast cancer are diagnosed every year in the United States, and it is estimated that one out of every eight women will develop breast cancer during her lifetime.

SUMMARY OF THE INVENTION

In general, the invention features a substantially pure preparation of NES1 polypeptide. Preferably, the NES1 polypeptide includes an amino acid sequence substantially identical to the amino acid sequence shown in FIG. 10 (SEQ ID NO: 1); and is derived from a mammal, for example, a human.

In related aspects, the invention features purified DNA (for example, cDNA) which includes a sequence (for example, a NES1 DNA sequence substantially identical to the sequence shown in FIG. 11; SEQ ID NO: 2) encoding a NES1 polypeptide (for example, a human NES1 polypeptide having a sequence substantially identical to the sequence shown in FIG. 10; SEQ ID NO: 1); a vector and a cell, each of which includes a purified NES1 DNA of the invention; and a method of producing a recombinant NES1 polypeptide involving providing a cell transformed with DNA encoding a NES1 polypeptide positioned for expression in the cell, culturing the transformed cell under conditions for expressing the DNA, and isolating the recombinant NES1 polypeptide. The invention further features recombinant NES1 polypeptide produced by such expression of a purified DNA of the invention, and substantially pure antibody that specifically recognizes and binds a NES1 polypeptide.

In addition, the invention features a method of diagnosing a mammal for the presence of a malignancy or an increased likelihood of developing a malignancy. The method involves measuring NES1 gene expression in a sample from the mammal, with a decrease in NES1 expression relative to a wild-type sample being an indication that the mammal has a malignancy or has an increased likelihood of developing a malignancy.

In preferred embodiments, the malignancy is a carcinoma; the sample includes an epithelial cell or a cell of epithelial origin; the sample includes a breast tissue cell; the sample includes a cervical tissue cell; the sample includes a prostate tissue cell; NES1 gene expression is measured by assaying the amount of NES1 polypeptide in the sample (for example, by immunological methods); and NES1 gene expression is measured by assaying the amount of NES1 mRNA in the sample (for example, by hybridization techniques using a NES1-specific nucleic acid sequence).

Kits for carrying out the above methods are also included in the invention. Such kits preferably include a substantially pure antibody that specifically recognizes and binds a NES1 polypeptide, and may also include means for detecting and quantitating antibody binding. Alternatively, the kit may include all or a fragment of a NES1 nucleic acid sequence useful for hybridization purposes, and may also include means for detecting and quantitating NES1 RNA hybridization.

In yet another related aspect, the invention features a method of diagnosing a mammal for the presence of a malignancy or an increased likelihood of developing a malignancy, involving isolating a sample of nucleic acid from the mammal and determining whether the nucleic acid includes a mutated NES1 gene, a NES1 mutation being an indication that the mammal has a malignancy or has an increased likelihood of developing a malignancy.

In preferred embodiments, the malignancy is a carcinoma; the nucleic acid sample is isolated from an epithelial cell or a cell of epithelial origin; the epithelial cell is a breast tissue cell; the epithelial cell is a cervical tissue cell; and the epithelial cell is a prostate tissue cell.

Kits for carrying out this method are also included in the invention. Such kits preferably include a wild-type NES1 nucleic acid sequence (for comparison with the sequence isolated from the mammal to be diagnosed) and may also include means for detecting a mismatch between the wild-type and sample NES1 sequences.

In yet another related aspect, the invention features a method of diagnosing a mammal for the presence of a malignancy or an increased likelihood of developing a malignancy, involving measuring NES1 protease activity in a sample from the mammal, a decrease in the NES1 protease activity relative to a wild-type sample being an indication that the mammal has a malignancy or has an increased likelihood of developing a malignancy.

In preferred embodiments, the malignancy is a carcinoma; the sample includes an epithelial cell or a cell of epithelial origin; the sample includes a breast tissue cell; the sample includes a cervical tissue cell; and the sample includes a prostate tissue cell.

Kits for carrying out this method are also included in the invention. Such a kit includes a substantially pure wild-type NES1 polypeptide (for example, a NES1 polypeptide including an amino acid sequence substantially identical to the amino acid sequence shown in FIG. 10; SEQ ID NO: 1)), and may also include means for measuring protease activity.

Moreover, the invention features a method of treating a mammal with a NES1-associated malignancy, involving administering to the mammal a transgene encoding a NES1 polypeptide.

In preferred embodiments, the transgene encodes a NES1 polypeptide including an amino acid sequence substantially identical to the amino acid sequence shown in FIG. 10 (SEQ ID NO: 1); the transgene is administered to the mammal at the site of the malignancy; the transgene is included in a viral vector (for example, a retrovirus, adenovirus, or adeno-associated virus vector); and the malignancy is a carcinoma (for example, a breast carcinoma, cervical carcinoma, or prostate carcinoma).

The invention also features a method of treating a mammal with a NES1-associated malignancy (for example, a carcinoma), involving administering to the mammal a NES1 polypeptide in an amount sufficient to inhibit growth of the malignancy, and further features a therapeutic composition having as an active ingredient a NES1 polypeptide, formulated in a physiologically-acceptable carrier.

In two other related aspects, the invention features methods of identifying NES1 modulatory compounds. The first method involves the identification of modulatory compounds that are capable of increasing the expression of a NES1 gene, involving (a) providing a cell expressing the NES1 gene; and (b) contacting the cell with a candidate compound, an increase in NES1 expression following contact with the candidate compound identifying a modulatory compound. The second method involves the identification of modulatory compounds which are capable of increasing NES1 protease activity, involving (a) providing a cell expressing the NES1 protease; and (b) contacting the cell with a candidate compound, an increase in NES1 protease activity following contact with the candidate compound identifying a modulatory compound.

In preferred embodiments of both methods, the NES1 gene encodes or the NES1 protease includes an amino acid sequence that is substantially identical to the amino acid sequence shown in FIG. 10 (SEQ ID NO: 1); the candidate compound is chosen from a tumor promoter, a differentiation agent, or a cytokine; the candidate compound is chosen from compounds known to act through a protein kinase C signal transduction pathway; and the candidate compound is chosen from diacylglycerol, retinoic acid, estradiol, di-butyryl cyclic AMP, forskolin, TGFβ, TNF, or IL1.

In a related aspect, the invention features a method of treating a mammal with a disease involving decreased expression of a NES1-encoding gene, involving administering to the patient a modulatory compound (for example, identified according to the above methods) in an amount effective to reduce the symptoms of the disease in the mammal. Preferably, the modulatory compound acts through a protein kinase C signal transduction pathway (for example, the compound is 4,8-phorbol-12-myristate-13-acetate).

In a final aspect, the invention features a NES1 protease. Preferably, the NES1 protease is a serine protease; and has an amino acid sequence substantially identical to the sequence shown in FIG. 10 (SEQ ID NO: 1). In a related aspect, the invention also features a method of cleaving a polypeptide involving contacting the polypeptide with a NES1 polypeptide (for example, a NES1 polypeptide having an amino acid sequence substantially identical to the sequence shown in FIG. 10 (SEQ ID NO: 1)) under conditions sufficient for cleavage.

By "NES1 polypeptide" is meant an amino acid sequence which is a cell cycle-regulated serine protease whose expression negatively correlates with the presence of malignant epithelial cells. Preferably, such a polypeptide has an amino acid sequence which is at least 45%, preferably 60%, and most preferably 85% or even 95% identical to the amino acid sequence of the NES1 protein of FIG. 10 (SEQ ID NO: 1).

By a "substantially identical" polypeptide sequence is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein).

Preferably, such a sequence is at least 85%, more preferably 90%, and most preferably 95% identical at the amino acid level to the sequence of FIG. 10 (SEQ ID NO: 1). For polypeptides, the length of comparison sequences will generally be at least 15 amino acids, preferably at least 20 amino acids, more preferably at least 25 amino acids, and most preferably at least 35 amino acids.

Homology is typically measured using sequence analysis software (e.g., Sequence Analysis Software Package of the Genetics Computer Group, University of Wisconsin Biotechnology Center, 1710 University Avenue, Madison, Wis.53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "protein" or "polypeptide" is meant any chain of amino acids, regardless of length or post-translational modification (e.g., glycosylation or phosphorylation).

By "substantially pure" is meant a preparation which is at least 60% by weight (dry weight) the compound of interest, e.g., the NES1 polypeptide or NES1-specific antibody. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 45%, more preferably 60%, and most preferably 85% identical at the amino acid level to the sequence of FIG. 10 (SEQ ID NO: 1). If nucleic acid sequences are compared a "substantially identical" nucleic acid sequence is one which is at least 85%, more preferably 90%, and most preferably 95% identical to the sequence of FIG. 11 (SEQ ID NO: 2). The length of nucleic acid sequence comparison will generally be at least 50 nucleotides, preferably at least 60 nucleotides, more preferably at least 75 nucleotides, and most preferably 110 nucleotides. Again, homology is typically measured using sequence analysis software (e.g., Sequence Analysis Software Package of the Genetics Computer Group, University of Wisconsin Biotechnology Center, 1710 University Avenue, Madison, Wis. 53705).

By "transformed cell" is meant a cell into which (or into an ancestor of which) has been introduced, by means of recombinant DNA techniques, a DNA molecule encoding (as used herein) NES1 protein.

By "positioned for expression" is meant that the DNA molecule is positioned adjacent to a DNA sequence which directs transcription and translation of the sequence (i.e., facilitates the production of NES1 protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds a NES1 polypeptide but which does not substantially recognize and bind other molecules in a sample (e.g., a biological sample) which naturally includes NES1 polypeptide. An antibody which "specifically binds" NES1 is sufficient to detect a NES1 protein product in such a biological sample using one or more of the standard immunological techniques available to those in the art (for example, Western blotting or immunoprecipitation).

By "malignancy" is meant any abnormal tissue that grows by cellular proliferation more rapidly than normal or that continues to grow after growth stimuli cease. Most malignancies show partial or complete lack of structural organization or functional coordination with surrounding normal tissue. A malignancy according to the invention is generally either locally invasive or metastatic.

By "relative to a wild-type sample" is meant either (a) relative to an equivalent tissue sample from an unaffected individual or (b) relative to an unaffected sample of similar tissue type from the mammal being diagnosed.

By "carcinoma" is meant any of the various types of malignancies derived from epithelial tissues. Carcinomas include, without limitation, malignancies arising in breast, cervix, prostate, skin, large intestine, lung/bronchi, liver, brain, kidney, ovary, uterus, stomach, esophagus, nasopharynx, larynx, or glandular tissues.

By a "cell of epithelial origin" is meant a cell (for example, a malignant cell) that, at some point in its life cycle, was an epithelial cell (i.e., a cell of the avascular layer that covers the free surface of the body, including, without limitation, the cutaneous, mucous, and serous layers, all glandular surfaces, and structures derived therefrom).

By "immunological methods" is meant any assay involving antibody-based detection techniques including, without limitation, Western blotting, immunoprecipitation, and direct and competitive ELISA and RIA techniques.

By "means for detecting" is meant any one or a series of components that sufficiently indicate a detection event of interest. Such means involve at least one label that may be assayed or observed, including, without limitation, radioactive, fluorescent, and chemiluminescent labels.

By "NES1 RNA" is meant messenger RNA transcribed from a NES1 DNA sequence.

By "hybridization techniques" is meant any detection assay involving specific interactions (based on complementarity) between nucleic acid strands, including DNA—DNA, RNA—RNA, and DNA-RNA interactions. Such hybridization techniques may, if desired, include a PCR amplification step.

By "protease activity" is meant, in this case, NES1-mediated cleavage at a specific amino acid sequence.

By "transgene" is meant a DNA sequence which is inserted by artifice into a cell and becomes a part of the genome of that cell and its progeny. Such a transgene may be partly or entirely heterologous to the cell.

By a "modulatory compound", as used herein, is meant any compound capable of either increasing NES1 expression (i.e., at the level of transcription, translation, or post-translation) or increasing NES1 protein activity (i.e., the amount of activity, for example, protease activity, per unit of NES1 protein).

By a "tumor promoter" is meant any compound capable of promoting the growth of a tumor initiated by another agent (i.e., by a tumor initiator). Tumor promoters include, without limitation, any phorbol ester that is capable of activating a protein kinase C pathway (for example, the compound TPA).

By a "differentiation agent" is meant any compound which, when added to cells in vitro or introduced into a mammal, result in a change in the phenotype of a cell or tissue, including the expression of one or more markers indicative of a particular stage in the cell's or tissue's life cycle. Differentiation agents include, without limitation, retinoic acid and cyclic AMP.

By a "cytokine" is meant any polypeptide that is normally secreted (for example, from a cell of hematopoietic origin) and that binds to a cell surface receptor, thereby inducing a biochemical or functional activity in that cell. Cytokines include, without limitation, interleukin-1, tumor necrosis factor, and transforming growth factor $\beta$.

By a "protein kinase C signal transduction pathway" is meant any cellular pathway involving mammalian protein kinase C and playing a role in translating extracellular signals into changes in gene expression.

Other features and advantages of the invention will be apparent from the following detailed description thereof, and from the claims.

DETAILED DESCRIPTION

The drawings will first briefly be described.

DESCRIPTION OF THE DRAWINGS

In FIG. 5A, 76N cells were synchronized by growth factor deprivation (Keyomarsi et al., Cancer Res. 51:3602–3609, 1991), released from synchrony by the addition of regular medium, and analyzed for NES1 mRNA.

In FIG. 7A, logarithmically-growing 76N cells were exposed to 20 Gy of irradiation and analyzed for mRNA expression at the indicated time points.

FIG. 9A and B (SEQ ID NOS: 7–11)are charts showing sequence comparisons.

FIG. 10 is the amino acid sequence (SEQ ID NO: 1) encoded by a NES1 cDNA.

FIG. 11 is the nucleic acid sequence (SEQ ID NO: 2) of a NES1 cDNA.

Figure 1:
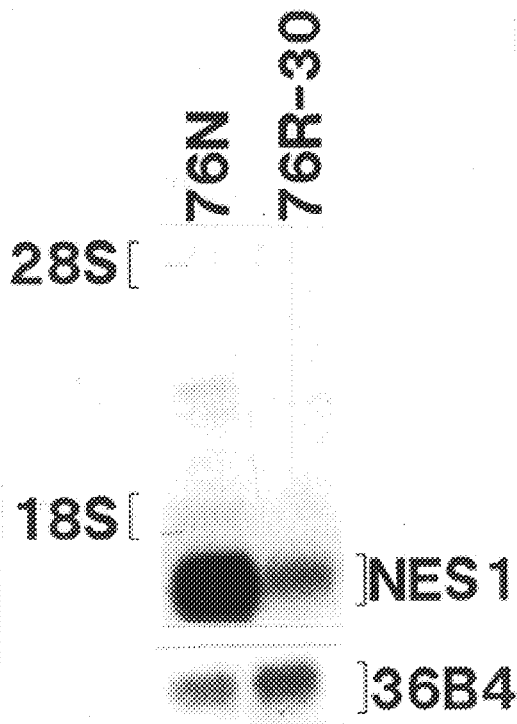
FIG. 1 is a photograph showing a Northern blot analysis of NES1 mRNA expression. Total cellular RNA (10 $\mu$g) from various cells (cell type designations indicated in parentheses are described in Table 1) was resolved on a 1.5% agarose-formaldehyde gel, transferred to a nylon membrane, and hybridized with a 0.4-kb NES1 probe. Locations of the ribosomal RNAs (28S, 4,850 bp; and 18S, 1,740 bp) are indicated. Note the drastic decrease in NES1 mRNA in the 76R-30 cells. 36B4 was used as a loading control.

There now follows a detailed description of the cloning and characterization of the NES1 cDNA and expression product. A radiation-transformed human mammary epithelial cell (MEC) line, 76R-30, was established by exposing a normal MEC strain, 76N, to fractionated y-irradiation. 76R-30 cells showed an early and complete loss of expression of a well characterized tumor suppressor gene product p53. Thus, 76N and 76R-30 represented a pair of isogenic cells providing a unique system to isolate novel genes that are involved in radiation-induced MEC transformation. Subtractive hybridization between 76N and 76R-30 cells led to the isolation of the novel NES1 gene, whose mRNA expression was dramatically decreased in 76R-30 cells. Significantly, NES1 mRNA was reduced by exposure of several MECs to fractionated y-irradiation. NES1 mRNA was either absent or drastically reduced in a majority of established breast cancer cell lines and markedly reduced when an immortal non-tumorigenic cell line was rendered tumorigenic by activated H-ras transfection. Furthermore, treatment of MECs with a phorbol ester, PMA, led to a significant increase in NES1 mRNA. Finally, the expression of NES1 mRNA was found to be cell cycle regulated. Sequencing of a NES1 cDNA clone revealed it to be a previously unknown protein with significant homology to serine proteases such as trypsin. Given these characteristics, NES1 is highly likely to be involved in maintenance of the untransformed state of mammary epithelial cells and perhaps all epithelial cells. Accordingly, NES1 provides an unusually useful diagnostic marker for detecting carcinomas as well as providing a genetic construct for gene therapy techniques.

Transformation of Normal Mammary Epithelial Cell Strain 76N by Fractionated Radiation To produce a transformed mammary epithelial cell line, a normal human MEC strain, 76N, was exposed to fractionated γ-irradiation (2 Gy/day) at a clinically used dose (30 Gy), and the immortal, morphologically-transformed cell line, 76R-30, was derived. These cells had reduced growth factor requirements and produced tumors in nude mice. Significantly, 76R-30 cells completely lacked the p53 tumor suppressor protein. Loss of p53 protein was due to deletion of one allele and a 26 bp deletion within the third intron of the second allele, which resulted in an abnormal splicing out of either the third or fourth exon from the mRNA. PCR with a mutation-specific primer showed that the intron 3 mutation was present in irradiated cells before selection for the immortal phenotype. 76R-30 cells did not exhibit $G_1$ cell cycle arrest in response to radiation, indicating a loss of p53-mediated function. Expression of the wild-type p53 gene in 76R-30 cells led to growth inhibition. Thus, loss of p53 protein appears to have contributed to the neoplastic transformation of these cells (Wazer et al., Mol. Cell. Biol. 14:2468–2478, 1994).

Cloning of the NES1 Gene

In order to isolate novel genes whose mRNA expression was up- or down-regulated during radiation-induced transformation of mammary epithelial cells, subtracted cDNA libraries from 76N (normal) MEC and the isogenic, radiation-transformed derivative 76R-30 were made in a γSHlox vector (Novagen, Madison, Wis.) (Palazzolo et al., Gene 88:25–36, 1990). Briefly, poly A⁺ RNA from each cell line was used to generate first strand cDNA, and RNA messages present in both cells were depleted by subtractive hybridization (i.e., 76N was subtracted against 76R-30 and vice versa). Between 1.4 and $2.9\times10^6$ primary recombinants were obtained and amplified to yield libraries with a titer of 1.8 to $2.2\times10^{10}$ pfu/ml. A 76NS library (i.e., 76N cDNA subtracted against 76R-30 RNA) was used for the isolation of the NES1 gene. A total of about 40,000 phages (2000/150 mm dishes) were plated, and duplicate filters were screened with $^{32}$p-labelled cDNA generated by reverse transcription of 76N and 76R-30 mRNA. Phages that gave higher signals with the 76N compared to the 76R-30 cDNA probe were plaque-purified by repeated screening at lower density. Cre recombinase-mediated site-specific recombination was used to obtain cDNA clones of interest in the plasmid form (Palazzolo et al., Gene 88:25–36, 1990). Using this approach, several cDNAs were isolated that preferentially hybridized to a labelled cDNA probe derived from 76N compared to 76R-30 cells. One partial cDNA, termed "NES1" (for Normal Epithelial Specific-1), was characterized in detail and used to carry out the following experiments.

Expression of the NES1 Gene in Normal Versus Radiation-Transformed Cells

A NES1 cDNA insert of 400 base pairs was isolated by digestion with EcoRI and HindIII (i.e., the enzymes used for cloning), labelled with $^{32}$p by the random-primer method, and used as a probe in Northern blots to detect relative mRNA expression in 76N and 76R-30 cells. As shown in FIG. 1, the 76N normal parent cells expressed abundant levels of a 1.6 kb mRNA. In contrast, radiation-transformed 76R-30 cells showed a dramatically reduced expression of NES1 mRNA. Thus, NES1 appears to be down-regulated at the mRNA level during radiation-induced transformation of 76N mammary cells.

Expression of NES1 in Normal, Immortalized, and Tumor Mammary Cells

Figure 2A:
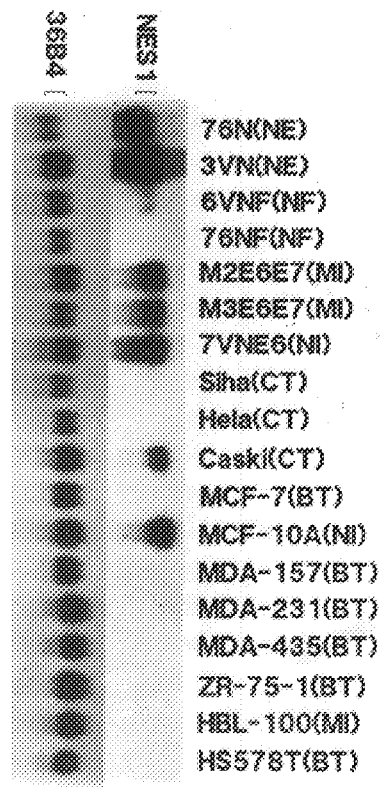
FIG. 2 is a photograph showing a Northern blot analysis of NES1 mRNA expression. Total cellular RNA (10 μg) from various cells (cell type designation indicated in parentheses are described in Table 1) was resolved on a 1.5% agarose-formaldehyde gel, transferred to a nylon membrane, and hybridized with a 0.4-kb NES1 probe. Note the drastic decrease in NES1 mRNA in 76R-30 cells and almost complete loss in most mammary tumor cell lines. 36B4 was used as a loading control.
Figure 2B:
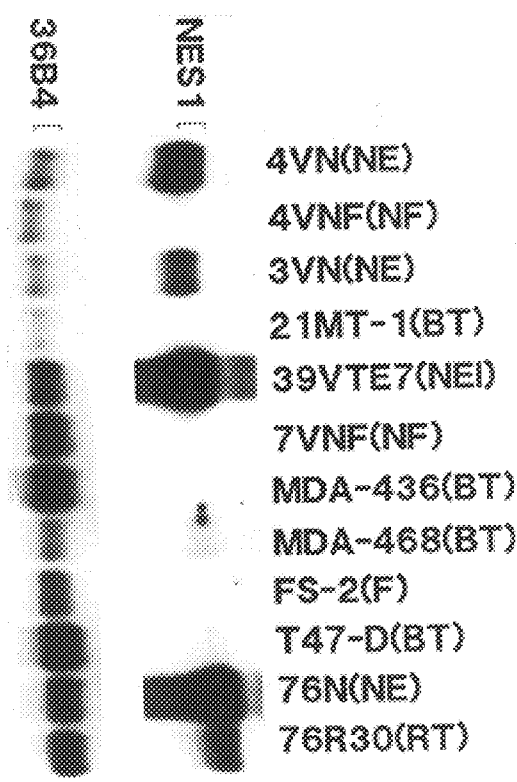

To further explore the expression of NES1 mRNA and its relationship to tumor progression, a number of normal MECs, mammary fibroblasts, immortalized MECs, and mammary tumor cell lines were analyzed by Northern blot analysis. These results are presented in FIG. 2 and summarized in Table 1.

TABLE 1

Relative NES1 mRNA Expression
in Human Mammary Epithelial and Other Cells

| Normal mammary epithelial cell strains (NE) | |
|---|---|
| 76N | ++++ |
| 3VN | +++++ |
| 4VN | ++++ |

| Normal mammary fibroblast cell strains (NF) | |
|---|---|
| 76NF | − |
| 4VNF | − |
| 6VNF | +[a] |
| 7VNF | − |

| Foreskin fibroblast cell strain | |
|---|---|
| FS-2 | − |

| Immortalized mammary epithelial cell lines | |
| HPV-16 E6 or E7-immortalized cells | |
| from mammoplasties (NI) | |
|---|---|
| 76E6 | ++++ |
| 7VNE6 | ++++ |
| 39VTE7 | ++++ |

| HPV-16 E6/E7-immortalized milk-derived | |
| cells (MI) | |
|---|---|
| M2E6E7 | +++ |
| M3E6E7 | +++ |

| Other immortal cells | |
|---|---|
| HBL-100 (transformed milk cells from ATCC) | − |

TABLE 1-continued

Relative NES1 mRNA Expression
in Human Mammary Epithelial and Other Cells

| Radiation-transformed cells (RT) | |
|---|---|
| 76R-30 | + |

| Breast tumor cell lines (BT) | |
| Estrogen receptor positive | |
|---|---|
| T-47D | − |
| ZR-75-1 | − |
| MCF-7 | − |

| Estrogen receptor negative | |
|---|---|
| 21PT* | +++ |
| 21NT* | +++ |
| 21MT-1* | −/+ |
| | (upon longer exposure) |
| 21MT-2* | +++ |
| MDA-MB-134 | − |
| MDA-MB-157 | − |
| MDA-MB-175 | − |
| MDA-MB-231 | − |
| MDA-MB-361 | − |
| MDA-MB-415 | − |
| MDA-MB-435 | − |
| MDA-MB-436 | − |
| MDA-MB-453 | − |
| MDA-MB-468 | + |
| Hs578T | − |
| BT-474 | − |
| BT-483 | − |
| BT-549 | − |
| ZR-75-30 | − |
| SK-BR-3 | − |

| Cervical carcinoma cell lines (CT) | |
|---|---|
| Siha | − |
| HeLa | − |
| Caski | ++ |

* These cell lines were derived from a single patient with breast cancer (Band et al., Cancer Res. 50:7351-7357, 1990).
[a] Due to epithelial cell contamination.

All normal and immortalized epithelial cells expressed high levels of NES1 mRNA, whereas all fibroblast cells failed to express it. Notably, all HPV-16 E6 or E7-immortalized mammary epithelial cells expressed NES1 mRNA levels comparable to normal MECs. Remarkably, however, a drastic decrease or complete loss of NES1 message was observed in all breast cancer cell lines examined, except for four lines (21PT, 21NT, 21MT-1, and 21MT-2) derived from a single patient (FIGS. 2, 7B, and 6) (Band et al., Cancer Res. 50:7351–7357, 1990). In addition, two out of three randomly selected cervical carcinoma cell lines showed no expression of the NES1 gene. Thus, NES1 mRNA expression appears to be down-regulated during tumorigenic progression and not by mere immortalization of mammary cells.

Expression of NES1 in Ras-Transformed Cells

Figure 3:
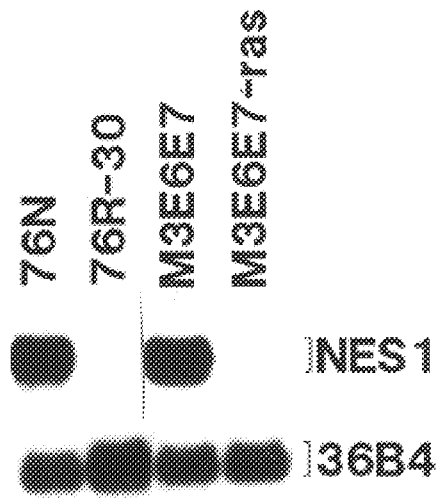
FIG. 3 is a photograph showing a Northern blot analysis of NES1 mRNA expression. Total cellular RNA (10 μg) from various cells (cell type designations indicated in parentheses are described in Table 1) was resolved on a 1.5% agarose-formaldehyde gel, transferred to a nylon membrane, and hybridized with a 0.4-kb NES1 probe. Note the drastic decrease in NES1 mRNA in 76R-30, and in ras-transformed immortalized milk epithelial cells. 36B4 was used as a loading control.

To further address the down-regulation of NES1 expression during tumorigenic transformation, the HPV-16 E6+E7-immortalized milk-derived MEC line (M3E6E7) was compared with its isogenic activated-ras-transfected tumorigenic derivative (M3E6E7-ras). Both cells were grown under identical conditions. The ras-transfected cells showed a dramatic reduction in NES1 expression as compared to the non-tumorigenic immortal parent cell (FIG. 3). This result confirms the down-regulation of NES1 expression during tumor progression.

Southern Blot Analysis of the NES1 Gene

Figure 4:
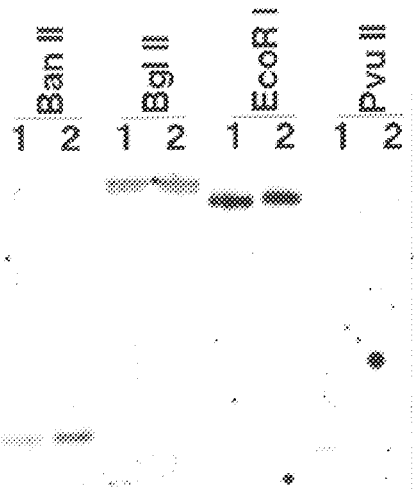
FIG. 4 is a photograph showing a Southern blot analysis of NES1 DNA. Genomic DNA from 76N or 76R-30 was digested with the indicated restriction enzymes, run on a 1.0% agarose gel, transferred to a nylon membrane, and hybridized with a 0.4-kb NES1 probe. Note that both cell lines show hybridizing bands of identical size and intensity.

In order to determine if the decrease or loss of NES1 mRNA expression in oncogenically-transformed cells was due to deletion or rearrangement of the gene, Southern blot analyses of BanII, BglII, EcoRI, or PvuII-digested genomic DNA isolated from 76N or 76R-30 were performed. As shown in FIG. 4, both cells showed identical hybridizing bands of equal intensity. Similarly, two other NES1 mRNA-negative cell lines MDA-MB-231 and MDA-MB-468 showed identical bands. Therefore, loss of NES1 mRNA expression does not appear to be due to any major deletion or rearrangement of the gene. However, this analysis does not exclude the presence of more subtle mutations that may lead to loss of expression.

Cell Cycle-Regulated Expression of the NES1 Gene

Figure 5A:
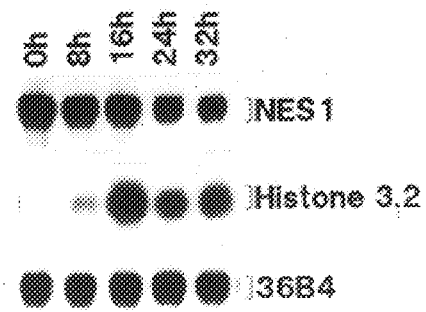
FIG. 5A and B show a photograph and a graph indicating the results of a cell cycle analysis of NES1 mRNA expression.
Figure 5B:
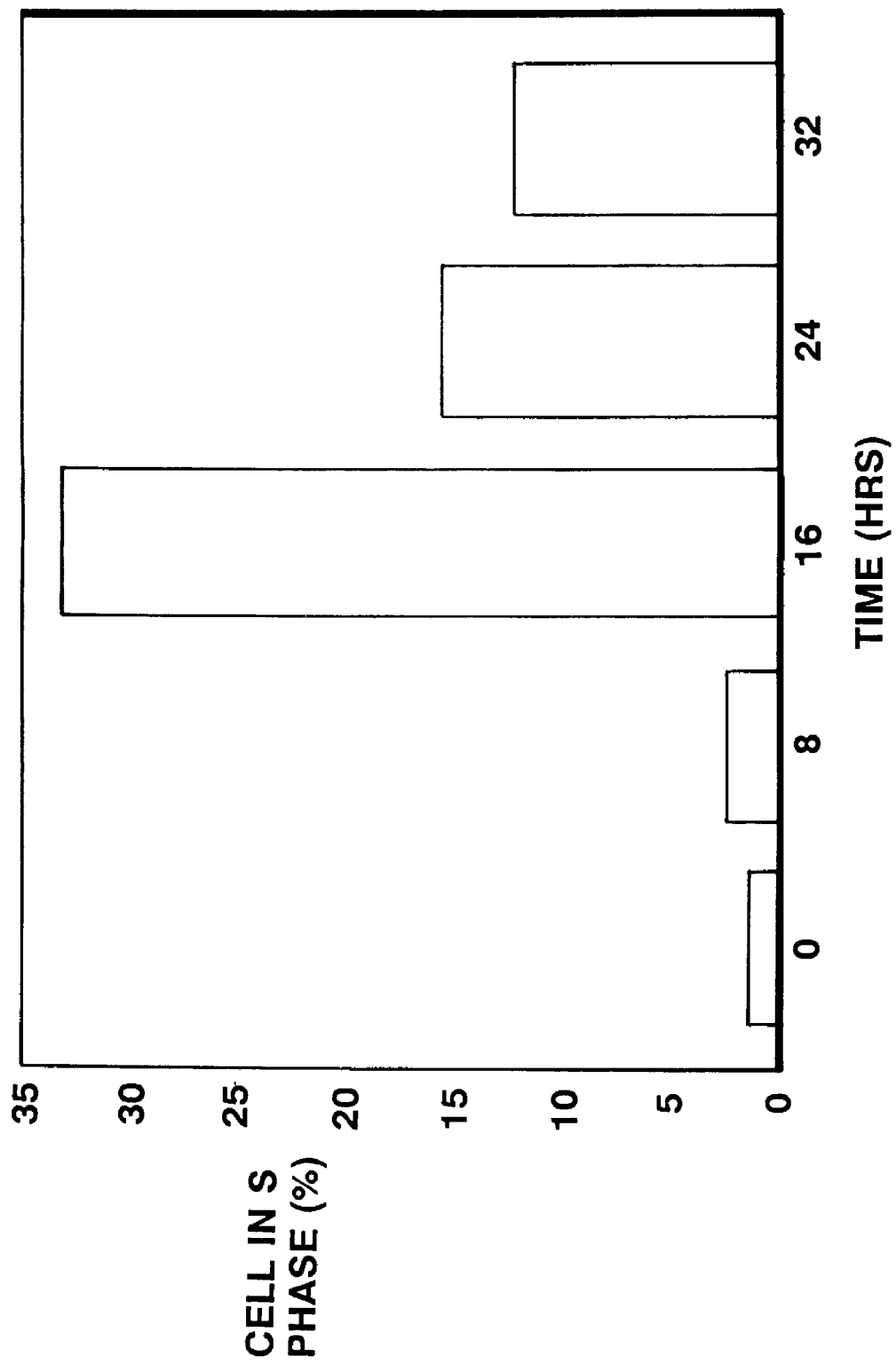
In FIG. 5B, this experiment was repeated, but cell cycle distribution was analyzed by propidium iodide FACS analysis (Wazer et al., Mol. Cell Biol. 14:2468–2478, 1994). Histone 3.2 was used as a positive control and 36B4 as a loading control.

Down-regulation of NES1 expression during tumorigenic transformation suggested that the gene may be regulated during the cell cycle. To assess this, we synchronized 76N normal MECs by growth factor deprivation and released them from synchrony by adding complete medium, using standard techniques (Keyomarsi et al., Cancer Res. 51:3602–3609, 1991). At various time points, cells were analyzed for DNA content (to determine cell cycle distribution), and another aliquot was used for mRNA isolation to analyze the expression of the NES1 gene. As shown in FIG. 5, a higher expression of NES1 was observed in cells arrested at $G_0/G_1$, and the expression decreased substantially as cells progressed toward late S phase and G2. In contrast, histone mRNA expression was essentially absent in arrested cells and highest at S phase, as expected (Gudas et al., Cell Growth & Diff. 5:295–304, 1994). These results indicated that expression of NES1 mRNA is cell cycle-regulated.

Cell Density-Regulated Expression of the NES1 Gene

Figure 6:
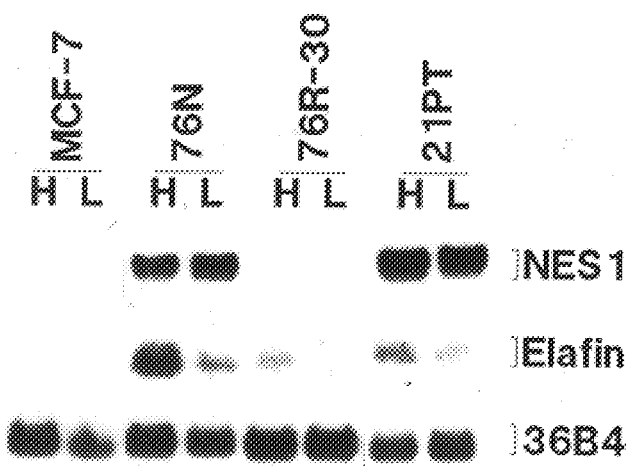
FIG. 6 is a photograph indicating the effect of cell density on NES1 mRNA expression. Cells were plated at either low ($2\times10^5$) or high ($2\times10^6$) densities and after 72 hours analyzed for NES1 mRNA as in FIG. 1. Note that there is no significant difference in NES1 mRNA expression. Elafin, a cell density-dependent gene, was used as a positive control and 36B4 as a loading control.

In view of the higher NES1 mRNA expression in the $G_0/G_1$ phase of the cell cycle, NES1 expression in relation to cell density was also analyzed. Four different cell lines that had shown either high (76N, 21PT), low (76R-30), or no (MCF-7) expression of the NES1 gene (Table 1) were selected, and the cells plated at low ($2 \times 10^5$) or high ($2 \times 10^6$) cell densities. After 72 hours, cells were harvested, and equal amounts of RNA were examined by Northern blotting. As shown in FIG. 6, no change in the expression of NES1 mRNA was observed between paired samples of cells grown at different cell densities. Notably, 76R-30 or MCF-7 cells did not express NES1 mRNA even at higher cell densities. Hybridization of the same blot with elafin (whose expression is density-dependent) showed a significant increase in cells grown at higher cell density (FIG. 6). The MCF-7 cell line lacked the expression of elafin mRNA.

Effect of Acute or Chronic γ-Irradiation on NES1 Expression

Figure 7A:
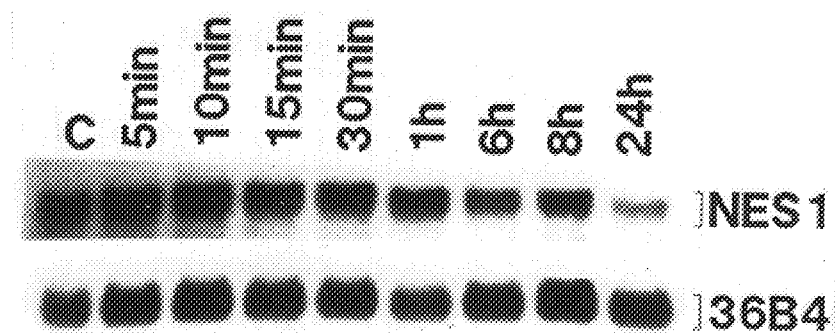
FIG. 7A and B are photographs showing the effect of acute or chronic treatment of y-irradiation on NES1 expression.

Identification of NES1 was based on down-regulation of its expression in radiation-transformed 76R-30 cells as compared to 76N normal parent cells. To determine if NESI down-regulation was a direct consequence of radiation-induced biochemical alterations, the effect of acute or chronic γ-irradiation on NES1 expression in MECs that were not grown in selection media was examined. Acute γ-irradiation (single dose of 20 Gy) did not significantly alter NES1 MRNA expression in 76N cells examined at early time points (i.e., from 5 minutes to 8 hours) (FIG. 7A). However, a reproducible decrease in NESI mRNA was observed at 24 hours after γ-irradiation.

Figure 7B:
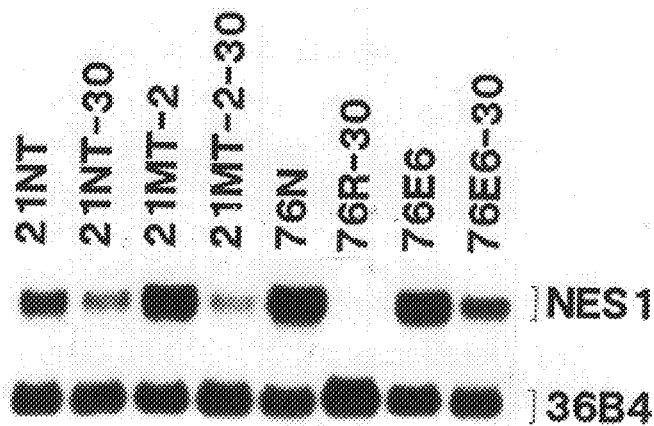
In FIG. 7B, for chronic irradiation, cells were treated with fractionated radiation (2 Gy/day until 30 Gy) and then compared for NES1 mRNA expression with paired control (untreated) cells. 76N and 76R-30 are shown for comparison. 36B4 was used as a loading control.

To assess the effect of chronic γ-irradiation, mRNA expression was examined in mammary epithelial cells that were either untreated or exposed to fractionated doses of γ-irradiation (2 Gy/day for a total of 30 Gy), similar to the doses used to derive the 76R-30 cells. 30 Gy irradiation of three independent cell lines, 21NT (a primary breast tumor cell line), 21MT-2 (a breast metastatic tumor cell line), and 76E6 (E6-immortalized 76N cells), showed significant decreases in NES1 mRNA compared to paired untreated control cells (FIG. 7B). Thus, NES1 expression is uniquely down-regulated by chronic exposure to γ-irradiation.

Effect of PMA Treatment on NES1 Expression

Figure 8:
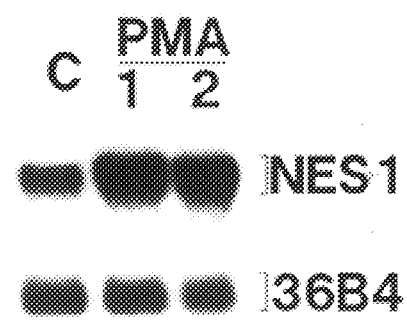
FIG. 8 is a photograph showing the effect of PMA on NES1 expression. Growing 76N cells were treated with 50 ng/ml (lane 1) or 100 ng/ml (lane 2) of PMA for 6 hours and then analyzed for NES1 mRNA expression. Note a significant increase in the levels of NES1 mRNA in PMA-treated samples.

To determine the biochemical pathways that regulate NES1 expression, the effect of the phorbol ester, 4,8-phorbol-12-myristate-13-acetate (PMA), which is known to activate protein kinase C was examined (Band et al., J. Cell Physiol. 138:106–114, 1989). Exposure of 76N cells to 50 or 100 ng/ml of PMA for 6 hours resulted in a significant increase in NES1 mRNA levels (FIG. 8). Because protein kinase C lies in signal transduction pathways downstream from a number of growth and differentiation factors, these results suggest that NES1 expression may be regulated by such stimuli. Accordingly, NES1 expression may be increased in response to other protein kinase C stimulators (for example, physiological activator diacylglycerol), differentiation agents (for example, retinoic acid, estradiol, di-butyryl cyclic AMP, and forskolin), or cytokines (for example, TGFβ, TNF, and IL1).

Isolation of a Full-Length NES1 cDNA

To clone the full-length NES1 cDNA, one of the longest cDNA fragments isolated as described above was used to provide subfragments near the 5' end and as the basis for oligonucleotides as further probes to screen the 76N cDNA library. The isolated cDNA clones were subjected to double-stranded dideoxy nucleotide sequencing by the Sequenase method (Wazer et al., Mol. Cell Biol. 14:2468–2478, 1994). Additional CDNA clones were obtained by screening a second 76N cDNA library in the pGAD10 vector (Clontech, Palo Alto, Calif.). Several independent cDNA clones were sequenced to assure that the 5' extensions did not represent artifactual ligations to irrelevant pieces of DNA (as is occasionally observed in cDNA libraries). Through this approach, a full length cDNA clone corresponding to NES1 mRNA was obtained and sequenced. The sequence is presented in FIG. 11 (SEQ ID NO: 2).

The 5' boundary of the cDNA is confirmed through the technique of primer-extension with specific oligonucleotide primers (i.e., primers bearing a sequence near the 5' end of the cDNA clone). In vitro translation of the NES1 fragment encompassing nucleotides 1–1069 using the In Vitro TNT coupled reticulocyte lysate system (Promega, Madison, Wis.) indicated a translation product of the predicted size (i.e., approximately 30 kDa).

Sequence of the NES1 Gene

To determine the nucleotide sequence of the NES1 cDNA, double-stranded sequencing was performed initially using two primers corresponding to the SP6 promoter (5'-CCG-CAG-ATT-TAG-GTG-ACA-C) (SEQ ID NO:3) and the T7 promoter (5'-GGC-CTC-TAA-TAC-GAC-TCA-C) (SEQ ID NO:4). Further full-length cDNA sequencing (in both directions) utilized two primers corresponding to the vector pGAD10 (i.e., the vector used for the second 76N cDNA library screen described above); these primers were of the following sequences: 5'-TAC-CAC- TAC-AAT-GGA-TG-3' (upstream primer) and 5'-GTT-GAA-GTG-AAC-TTG-CGG-GC-3' (downstream primer), as well as 12 NES1 sense primers (corresponding to nucleotides 6–22, 72–91, 128–145, 196–213, 344–360, 484–500, 634–650, 723–739, 851–867, 998–1116, 1125–1141, and 1253–1269) and 10 NES1 antisense primers (corresponding to nucleotides 1392–1377, 1294–1277, 1201–1185, 1086–1069, 917–899, 807–789, 674–657, 516–488, 292–275, and 176–161). Comparison of the cDNA sequence to the GENBANK database revealed no exact match, indicating that NES1 was a novel gene. The nucleotide sequence revealed an open reading frame of 277 amino acids followed by a stop codon (FIG. 11; SEQ ID NO: 2). A polyadenylation signal (ATATAA) was observed near the 3' end of the cDNA, indicating that this represents the 3' untranslated region.

Database comparison revealed NES1 to be highly homologous to members of the serine protease family at both the nucleotide (including the 3'-untranslated sequences) and amino acid levels (Table 2 and FIG. 9B).

TABLE 2

Amino Acid Homology of NES1 to Serine Proteases

| Serine Protease | % Similarity | % Identity |
| --- | --- | --- |
| Human brain trypsinogen IVb | 58 | 36 |
| Human pancreatic trypsinogen III | 60 | 37 |
| Dog pancreatic trypsinogen | 61 | 42 |
| Mouse preprotrypsin | 63 | 42 |
| Rat preprotrypsinogen IV | 59 | 39 |
| Xenopus pancreatic trypsin | 59 | 40 |
| Salmon salar trypsin II | 61 | 41 |
| Mouse nerve growth factor | 57 | 36 |
| Human hepatocyte growth factor | 53 | 34 |

In this table, % similarity indicates identical residues plus conservative substitutions.

Among the examples shown, 34–42% identity and 53–63% similarity (including conservative substitutions) to different serine proteases was observed. In addition, all important residues were conserved (Table 2 and FIG. 9B). In particular NES1 bears a conserved SDSGG sequence around the serine in the active site and other residues critical for substrate binding and specificity (FIG. 9 A and B). This sequence information indicates NES1 is a novel serine protease.

NES1 Protein Expression

In general, NES1 proteins according to the invention may be produced by transformation of a suitable host cell with all or part of a NES1-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The NES1 protein may be produced in a prokaryotic host (e.g., *E. coli*) or in a eukaryotic host (e.g., Saccharomyces cerevisiae, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Pal Alto, Calif.). If desired, this system may be used in conjunction with other protein expression techniques, for example, the myc tag approach described by Evan et al. (Mol. Cell Biol. 5:3610–3616, 1985).

Alternatively, a NES1 protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the NES1 protein is cloned into an expression vector which includes the dihydrofolate reductase (DHFR) gene. Integration of the plasmid and, therefore, the NES1 protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant NES1 protein is expressed, it is isolated, e.g., using affinity chromatography. In one example, an anti-NES1 protein antibody (e.g., produced as described herein) may be attached to a column and used to isolate the NES1 protein. Lysis and fractionation of NES1 protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short NES1 protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful NES1 fragments or analogs (described herein).

Anti-NES1 Antibodies

To generate NES1-specific antibodies, a NES1 coding sequence (i.e., amino acids 180–276) was expressed as a C-terminal fusion with glutathione S-transferase (GST) (Smith et al., Gene 67:31–40, 1988). The fusion protein (which was shown to be of the predicted size) was purified on glutathione-Sepharose beads, eluted with glutathione cleaved with thrombin (at the engineered cleavage site), and purified to the degree necessary for immunization of rabbits. Primary immunizations are carried out with Freund's complete adjuvant and subsequent immunizations with Freund's incomplete adjuvant. Antibody titres are monitored by Western blot and immunoprecipitation analyses using the thrombin-cleaved NES1 protein fragment of the GST-NES1 fusion protein. Immune sera are affinity purified using CNBr-Sepharose-coupled NES1 protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of NES1 may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using NES1 expressed as a GST fusion protein.

Alternatively, monoclonal antibodies may be prepared using the NES1 proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific NES1 recognition by Western blot or immunoprecipitation analysis (by the methods described in Ausubel et al., supra). Antibodies which specifically recognize NES1 are considered to be useful in the invention; such antibodies may be used, e.g., in an immunoassay to monitor the level of NES1 produced by a mammal (for example, to determine the amount or subcellular location of NES1).

Preferably, antibodies of the invention are produced using fragments of the NES1 protein which lie outside highly conserved regions and appear likely to be antigenic, by criteria such as high frequency of charged residues (for example, amino acids 121–137 or amino acids 1–20 of FIG. 10; SEQ ID NO: 1). In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Characterization of the Protease Activity of NES1

The amino acid sequence predicted by the NES1 cDNA shows considerable amino acid homology with trypsin-like serine proteases (FIG. 9A and B). In particular, the region of homology includes all of the amino acids of the protease catalytic triad and specificity pocket.

To directly characterize this protease activity, NES1 is expressed as a recombinant protein in bacteria using the pETvector (i.e., in which the protein is expressed untagged or tagged with gene 10 for further purification) (available from Novagen, Madison, Wis.) or the pGEX2T vector (i.e., as a GST fusion protein) (available from Pharmacia, Piscataway, N.J.). If bacterially expressed protein is insoluble or degraded, a baculovirus expression system in Sf9 insect cells is also available (for example, the expression vector and cell lines available from InVitrogen, San Diego, Calif.). In each case, the protein is partially purified, for example, by affinity separation (for example, using glutathione-Sepharose or anti-gene 10 monoclonal antibody). Alternatively, the NES1 gene is tagged with an anti-myc monoclonal antibody (gE10, American Type Culture Collection, Rockville, Md.) epitope or Histidine Tag (HisTag, InVitrogen, San Diego, Calif.), or is purified biochemically (e.g., by gel filtration/ion exchange chromatography). The purified protein is tested for biological activity, using immunoprecipitated material from 76N cells or transfected MECs (see above) as controls in parallel experiments.

Protease activity is assayed based on the standard technology employed to determine the protease activity and specificity of other serine proteases (Smyth et al., J. Biol. Chem. 267:24418–24425, 1992). For example, assays may be used that are based on small thiobenzylester peptide substrates. Protease activity is detected by reacting the thiobenzyl (Bzi) leaving group with 5,5'-dithiobis-(2-nitrobenzoic acid) (DTNB) (Sigma, St. Louis, Mo.) (detected at O. D. 410 nm.) or with 4,4'-dithiodipyridine to release thiopyridone (detected at O. D. 324). Protease activity directed to particular peptide linkages is determined by the use of various substrates. For example, the following commercially available or synthesized substrates allow determination of most serine protease specificities: BOC-Ala-Ala-Met-SBzl (Met-ase activity); Suc-Phe-Leu-Phe-SBzl (chymase activity); Z-Ar-SBzl (tryptase activity); and BOC-Ala-Ala-AsP-SBzl (Asp-ase activity) (Boehringer Mannheim, Indianapolis, Ind.). Typically these assays are done by kinetic measurement of substrate hydrolysis (as an increase in O. D. due to the leaving group reacting with DTNB or dithiopyridine), either on a spectrophotometer or microplate reader.

In one particular example, for BLT esterase activity, 50 $\mu$l of sample is added to 100 $\mu$l of 1 mM DTNB, made in 10 mM HEPES, and 1 mM $CaCl_2$, 1 mM $MgCl_2$, pH 7.2. The reaction is initiated by the addition of 50 $\mu$l of BLT to a final concentration of 500 $\mu$M. The rate of hydrolysis is measured by an increase of O. D. at 410 nm. As controls, sample and DTNB alone or sample and substrate alone are also run. Other activities are similarly determined under buffer conditions optimal for those activities (Smyth et al., J. Biol. Chem. 267:24418–24425, 1992). Using this approach, NES1 protease activity and specificity are determined.

As a protease, NES1 is used in accordance with any standard protease technique. For example, NES1 may be used to cleave a polypeptide in preparation for protein microsequencing or may be used to specifically cleave a fusion protein to release a polypeptide of interest.

Identification and Administration of Molecules that Modulate NES1 Protein Expression Isolation of the NES1 cDNA also facilitates the identification of molecules which increase or decrease NESI expression. According to one approach, candidate molecules are added at varying concentrations to the culture medium of cells expressing NES1 mRNA. NES1 expression is then measured, for example, by standard Northern blot analysis (Ausubel et al., supra) using a NES1 cDNA (or cDNA fragment) as a hybridization probe. The level of NES1 expression in the presence of the candidate molecule is compared to the level measured for the same cells in the same culture medium but in the absence of the candidate molecule.

If desired, the effect of candidate modulators on expression may, in the alternative, be measured at the level of NES1 protein production using the same general approach and standard immunological detection techniques, such as Western blotting or immunoprecipitation with a NES1-specific antibody (for example, the NES1 antibody described herein).

Candidate modulators may be purified (or substantially purified) molecules or may be one component of a mixture of compounds (e.g., an extract or supernatant obtained from cells; Ausubel et al., supra). In a mixed compound assay, NES1 expression is tested against progressively smaller subsets of the candidate compound pool (e.g., produced by standard purification techniques, e.g., HPLC or FPLC) until a single compound or minimal compound mixture is demonstrated to modulate NES1 expression.

Alternatively, or in addition, candidate compounds may be screened for those which modulate NES1 protease activity. In this approach, protease activity in the presence of a candidate compound is compared to protease activity in its absence, under equivalent conditions. Again, such a screen may begin with a pool of candidate compounds, from which one or more useful modulator compounds are isolated in a step-wise fashion. Protease activity may be measured by any standard assay, for example, those described herein.

Candidate NES1 modulators include peptide as well as non-peptide molecules (e.g., peptide or non-peptide molecules found, e.g., in a cell extract, mammalian serum, or growth medium on which mammalian cells have been cultured). Particularly useful modulators of NES1 expression include tumor promoters, for example, those acting through a protein kinase C pathway (for example, physiological activator ,diacylglycerol), differentiation agents (for example, retinoic acid, estradiol, di-butyryl cyclic AMP, and forskolin), and cytokines (for example, TGFβ, TNF, and IL-1).

A molecule which promotes an increase in NES1 expression or NES1 protease activity is considered particularly useful in the invention; such a molecule may be used, for example, as a therapeutic to increase cellular levels of NES1 and thereby exploit NES1's protective anti-cancer effects.

Modulators found to be effective at the level of NES1 expression or activity may be confirmed as useful in animal models and, if successful, may be used as anti-cancer therapeutics.

A NES1 modulator may be administered with a pharmaceutically-acceptable diluent, carrier, or excipient, in unit dosage form. Conventional pharmaceutical practice may be employed to provide suitable formulations or compositions to administer NES1 to patients suffering from or presymptomatic for a NES1-associated carcinoma. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for NES1 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a NES1 modulatory compound may be combined with more traditional cancer therapies such as surgery, radiation, or chemotherapy.

Detection of A Malignant Condition

NES1 polypeptides and nucleic acid sequences find diagnostic use in the detection or monitoring of cancerous conditions. In particular, because NES1 is involved in the control of cell division and because the absence of NES1 correlates with the development of carcinomas in humans, a decrease in the level of NESI production provides an indication of a malignant or pre-malignant condition. Levels of NES1 expression may be assayed by any standard technique. For example, its expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H.A. Ehrlich, Stockton Press, NY; and Yap and McGee, Nucl. Acids. Res. 19:4294, 1991).

Alternatively, a patient sample may be analyzed for one or more mutations in the NES1 sequence using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant NES1 detection, and each is well known in the art; examples of particular techniques are described, without limitation, in Orita et al., Proc. Natl. Acad. Sci. USA 86:2766–2770, 1989; and Sheffield et al., Proc. Natl. Acad. Sci. USA 86:232–236, 1989).

In yet another approach, immunoassays are used to detect or monitor NES1 protein in a biological sample. NES1-specific polyclonal or monoclonal antibodies (produced as described above) may be used in any standard immunoassay format (e.g., ELISA, Western blot, or RIA assay) to measure NES1 polypeptide levels; again comparison is to wild-type NES1 levels, and a decrease in NES1 production is indicative of a malignant condition. Examples of immunoassays are described, e.g., in Ausubel et al., supra. Immunohistochemical techniques may also be utilized for NES1 detection. For example, a tissue sample may be obtained from a patient, and a section stained for the presence of NES1 using an anti-NES1 antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of NES1 protein production (for example, by immunological techniques) and also includes a nucleic acid-based detection technique designed to identify more subtle NES1 mutations (for example, point mutations). As described above, a number of mismatch detection assays are available to those skilled in the art, and any preferred technique may be used (see above). By this approach, mutations in NES1 may be detected that either result in loss of NES1 expression or loss of NES1 biological activity. In a variation of this combined diagnostic method, NES1 biological activity is measured as protease activity using any appropriate protease assay system (for example, those described above).

Mismatch detection assays also provide the opportunity to diagnose a NES1-mediated predisposition to carcinomas. For example, a patient heterozygous for NES1 may show no clinical symptoms and yet possess a higher than normal probability of developing one or more types of carcinomas. Given this diagnosis, a patient may take precautions to minimize their exposure to adverse environmental factors (for example, to reduce exposure to radiation) and to carefully monitor their medical condition (for example, through frequent physical examinations). This type of NES1 diagnostic approach may also be used to detect NES1 mutations in prenatal screens.

The NES1 diagnostic assays described above may be carried out using any biological sample (for example, any biopsy sample or bodily fluid or tissue) in which NES1 is normally expressed (for example, the breast or cervix). Identification of a mutant NES1 gene may also be assayed using these sources for test samples. Alternatively, a NES1 mutation, particularly as part of a diagnosis for predisposition to NES1-associated malignancies, may be tested using a DNA sample from any cell, for example, by mismatch detection techniques; preferably, the DNA sample is subjected to PCR amplification prior to analysis.

Identification of the Subcellular Location of Cell Cycle Control Proteins

The NES1 polypeptide is also useful for identifying that compartment of a mammalian cell where important cell division control functions occur. Antibodies specific for NES1 may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

NES1 Therapy

Because expression of NES1 correlates with proper human epithelial cell division, the NES1 gene also finds use in anti-cancer gene therapy. In particular, to cure a NES1-deficient carcinoma cell, a functional NES1 gene may be introduced into cells at the site of a tumor.

Retroviral vectors, adenoviral vectors, adeno-associated viral vectors, or other viral vectors with the appropriate tropism for NES1-expressing cells (for example, epithelial cells) may be used as a gene transfer delivery system for a therapeutic NES1 gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into malignant cells. For example, NES1 may be introduced into a carcinoma cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic NES-b 1DNA construct is preferably applied to the site of the malignancy (for example, by injection), but may also be applied to tissue in the vicinity of the malignancy or even to a blood vessel supplying the malignancy.

In the gene therapy constructs, NES1 cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in epithelial cells may be used to direct NES1 expression. Such enhancers include, without limitation, the keratin or casein enhancers which are particularly useful for breast cell NES1 expression.

Alternatively, if a NES1 genomic clone is utilized as a therapeutic construct (for example, following its isolation by hybridization with the NES1 cDNA described above), NES1 expression is regulated by its cognate regulatory sequences or, if desired, by regulatory sequences derived from a heterologous source, e.g., any of the promoters or regulatory elements described above.

Less preferably, NES1 gene therapy is accomplished by direct administration of the NES1 mRNA to a malignancy. This mRNA may be produced and isolated by any standard technique, but is most readily produced by in vitro transcription using a NES1 cDNA under the control of a high efficiency promoter (e.g., the T7 promoter). Administration of NES1 mRNA to malignant cells is carried out by any of the methods for direct nucleic acid administration described above.

Ideally, the production of NES1 protein by any gene therapeutic approach described above results in a cellular level of NES1 that is at least equivalent to the normal, cellular level of NES1 in an unaffected individual.

Treatment by any NES1-mediated gene therapy approach may be combined with more traditional cancer therapies such as surgery, radiation, or chemotherapy.

Another therapeutic approach included within the invention involves direct administration of recombinant NES1 protein, either to the site of a malignancy (for example, by injection) or systemically by any conventional recombinant protein administration technique. The actual dosage of NESI 20 depends on a number of factors, including the size and health of the individual patient, but, generally, between 0.1 mg and 10 mg inclusive are administered per day to an adult in any pharmaceutically-acceptable formulation.

Preventive Carcinoma Therapy

In a patient diagnosed to be heterozygous for NESI or to be susceptible to NES1 mutations (even if those mutations do not yet result in loss of NES1 biological activity), any of the above therapies may be administered before the occurrence of a malignancy. In particular, compounds shown to increase NES1 expression or NES1 biological activity may be administered by any standard dosage and route of administration (see above).

Alternatively, gene therapy using a NES1 expression construct may be undertaken to reverse the cell defect prior to the development of additional NES1 mutations.

The methods of the instant invention may be used to reduce or diagnose the disorders described herein in any mammal, for example, humans, domestic pets, or livestock. Where a non-human mammal is treated or diagnosed, the NES1 polypeptide, nucleic acid, or antibody employed is preferably specific for that species.

OTHER EMBODIMENTS

In other embodiments, the invention includes any protein which is substantially identical to a human NES1 polypeptide (FIG. 10; SEQ ID NO:1); such homologs include other substantially pure naturally-occurring mammalian NES1 proteins as well as allelic variants; natural mutants; induced mutants; proteins encoded by DNA that hybridizes to the NES1 DNA sequence of FIG. 11 (SEQ ID NO: 2) under high stringency conditions or, less preferably, under low stringency conditions (e.g., washing at 2× SSC at 40° C. with a probe length of at least 40 nucleotides); and proteins specifically bound by antisera directed to a NES1 polypeptide. The term also includes chimeric polypeptides that include a NES1 portion.

The invention further includes analogs of any naturally-occurring NES1 polypeptide. Analogs can differ from the naturally-occurring NES1 protein by amino acid sequence differences, by post-translational modifications, or by both. Analogs of the invention will generally exhibit at least 85%, more preferably 90%, and most preferably 95% or even 99% identity with all or part of a naturally-occurring NES1 amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring NES1 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloninq: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes NES1 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of NES1 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a NES1 nucleic acid or amino acid sequence in a sample to be diagnosed. Particularly useful NES1 fragments for this purpose include, without limitation, amino acids 1–48 and amino acids 120–136 of FIG. 10; SEQ ID NO: 1. Preferable fragments also include those fragments which facilitate NES1-mediated proteolysis of target peptides, for example, fragments encompassing the catalytic triad important for substrate binding; these fragments include, without limitation, amino acids 86–245 and amino acids 42–245 of FIG. 10.

All publications and patent applications mentioned in this specification are herein incorporated by reference to the same extent as if each independent publication or patent application was specifically and individually indicated to be incorporated by reference.

Other embodiments are within the following claims.

What is claimed is:

1. A method of identifying a modulatory compound which is capable of increasing the expression of a Normal Epithelial Specific 1 (NES1) gene, said NES1 gene encoding a polypeptide having the sequence set forth in FIG. 10 (SEQ ID NO: 1), said method comprising (a) providing a cell expressing said NES1 gene, and (b) contacting said cell with a candidate compound, an increase in said NES1 expression following contact with said candidate compound identifying a modulatory compound.

2. A method of identifying a modulatory compound which is capable of increasing NES1 protease activity, wherein said NES1 protease has the sequence set forth in FIG. 10 (SEQ ID NO: 1), said method comprising (a) providing a cell expressing said NES1 protease; and (b) contacting said cell with a candidate compound, an increase in said NES1 protease activity following contact with said candidate compound identifying a modulatory compound.

3. The method of claims 1 or 2, wherein said candidate compound is chosen from a tumor promoter, a differentiation agent, or a cytokine.

4. The method of claim 3, wherein said candidate compound acts through a protein kinase C signal transduction pathway.

5. The method of claim 4, wherein said candidate compound is selected from the group consisting of diacylglycerol, retinoic acid, estradiol, di-butyryl cyclic adenosine monophosphate, forskolin, transforming growth factor beta, tumor necrosis factor, and interleukin 1.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 276 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Arg | Ala | Pro | His | Leu | His | Leu | Ser | Ala | Ala | Ser | Gly | Ala | Arg | Ala |
| 1 | | | | 5 | | | | | 10 | | | | | 15 | |
| Leu | Ala | Lys | Leu | Leu | Pro | Leu | Leu | Met | Ala | Gln | Leu | Trp | Ala | Ala | Glu |
| | | | 20 | | | | | 25 | | | | | 30 | | |
| Ala | Ala | Leu | Leu | Pro | Gln | Asn | Asp | Thr | Arg | Leu | Asp | Pro | Glu | Ala | Tyr |
| | | 35 | | | | | 40 | | | | | 45 | | | |
| Gly | Ala | Pro | Cys | Ala | Arg | Gly | Ser | Gln | Pro | Trp | Gln | Val | Ser | Leu | Phe |
| | 50 | | | | | 55 | | | | | 60 | | | | |
| Asn | Gly | Leu | Ser | Phe | His | Cys | Ala | Gly | Val | Leu | Val | Asp | Gln | Ser | Trp |
| 65 | | | | | 70 | | | | | 75 | | | | | 80 |
| Val | Leu | Thr | Ala | Ala | His | Cys | Gly | Asn | Lys | Pro | Leu | Trp | Ala | Arg | Val |
| | | | | 85 | | | | | 90 | | | | | 95 | |

| | | | | | | | | | | | | | | |
|---|---|---|---|---|---|---|---|---|---|---|---|---|---|---|
|  | Gly | Asp | Asp | His<br>100 | Leu | Leu | Leu | Leu | Gln<br>105 | Gly | Glu | Gln | Leu<br>110 | Arg | Arg | Thr |
|  | Thr | Arg | Ser<br>115 | Val | Val | His | Pro<br>120 | Lys | Tyr | His | Gln | Gly<br>125 | Ser | Gly | Pro | Ile |
|  | Leu | Pro<br>130 | Arg | Arg | Thr | Asp | Glu<br>135 | His | Asp | Leu | Met | Leu<br>140 | Leu | Lys | Leu | Ala |
|  | Arg<br>145 | Pro | Val | Val | Pro | Gly<br>150 | Pro | Arg | Val | Arg | Ala<br>155 | Leu | Gln | Leu | Pro | Tyr<br>160 |
|  | Arg | Cys | Ala | Gln | Pro<br>165 | Gly | Asp | Gln | Cys | Gln<br>170 | Val | Ala | Gly | Trp | Gly<br>175 | Thr |
|  | Thr | Ala | Ala | Arg<br>180 | Arg | Val | Lys | Tyr | Asn<br>185 | Lys | Gly | Leu | Thr<br>190 | Cys | Ser | Ser |
|  | Ile | Thr | Ile<br>195 | Leu | Ser | Pro | Lys | Glu<br>200 | Cys | Glu | Val | Phe | Tyr<br>205 | Pro | Gly | Val |
|  | Val | Thr<br>210 | Asn | Asn | Met | Ile | Cys<br>215 | Ala | Gly | Leu | Asp | Arg<br>220 | Gly | Gln | Asp | Pro |
|  | Cys<br>225 | Gln | Ser | Asp | Ser | Gly<br>230 | Gly | Pro | Leu | Val | Cys<br>235 | Asp | Glu | Thr | Leu | Gln<br>240 |
|  | Gly | Ile | Leu | Ser | Trp<br>245 | Gly | Val | Tyr | Pro | Cys<br>250 | Gly | Ser | Ala | Gln | His<br>255 | Pro |
|  | Ala | Val | Tyr | Thr<br>260 | Gln | Ile | Cys | Lys | Tyr<br>265 | Met | Ser | Trp | Ile<br>270 | Asn | Lys | Val |
|  | Ile | Arg | Ser<br>275 | Asn | | | | | | | | | | | | |

(2) INFORMATION FOR SEQ ID NO:2:

(i) SEQUENCE CHARACTERISTICS:
        (A) LENGTH: 1454 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
ACCAGCGGCA GACCACAGGC AGGGCAGAGG CACGTCTGGG TCCCCTCCCT CCTTCCTATC      60
GGCGACTCCC AGATCCTGGC CATGAGAGCT CCGCACCTCC ACCTCTCCGC CGCCTCTGGC     120
GCCCGGGCTC TGGCGAAGCT GCTGCCGCTG CTGATGGCGC AACTCTGGGC CGCAGAGGCG     180
GCGCTGCTCC CCCAAAACGA CACGCGCTTG GACCCCGAAG CCTATGGCGC CCCGTGCGCG     240
CGCGGCTCGC AGCCCTGGCA GGTCTCGCTC TTCAACGGCC TCTCGTTCCA CTGCGCGGGT     300
GTCCTGGTGG ACCAGAGTTG GGTGCTGACG GCCGCGCACT GCGGAAACAA GCCACTGTGG     360
GCTCGAGTAG GGATGATCA CCTGCTGCTT CTTCAGGGCG AGCAGCTCCG CCGGACGACT     420
CGCTCTGTTG TCCATCCCAA GTACCACCAG GGCTCAGGCC CCATCCTGCC AAGGCGAACG     480
GATGAGCACG ATCTCATGTT GCTAAAGCTG GCCAGGCCCG TAGTGCCGGG GCCCCGCGTC     540
CGGGCCCTGC AGCTTCCCTA CCGCTGTGCT CAGCCCGGAG ACCAGTGCCA GGTTGCTGGC     600
TGGGGCACCA CGGCCGCCCG GAGAGTGAAG TACAACAAGG GCCTGACCTG CTCCAGCATC     660
ACTATCCTGA GCCCTAAAGA GTGTGAGGTC TTCTACCCTG GCGTGGTCAC CAACAACATG     720
ATATGTGCTG GACTGGACCG GGGCCAGGAC CCTTGCCAGA GTGACTCTGG AGGCCCCTG     780
GTCTGTGACG AGACCCTCCA AGGCATCCTC TCGTGGGGTG TTTACCCCTG TGGCTCTGCC     840
CAGCATCCAG CTGTCTACAC CCAGATCTGC AAATACATGT CCTGGATCAA TAAAGTCATA     900
CGCTCCAACT GATCCAGATG CTACGCTCCA GCTGATCCAG ATGTTATGCT CCTGCTGATC     960
```

-continued

```
CAGATGCCCA  GAGGCTCCAT  CGTCCATCCT  CTTCCTCCCC  AGTCGGCTGA  ACTCTCCCT   1020

TGTCTGCACT  GTTCAAACCT  CTGCCGCCCT  CCACACCTCT  AAACATCTCC  CCTCTCACCT  1080

CATTCCCCCA  CCTATCCCCA  TTCTCTGCCT  GTACTGAAGC  TGAAATGCAG  GAAGTGGTGG  1140

CAAAGGTTTA  TTCCAGAGAA  GCCAGGAAGC  CGGTCATCAC  CCAGCCTCTG  AGAGCAGTTA  1200

CTGGGGTCAC  CCAACCTGAC  TTCCTCTGCC  ACTCCCCGCT  GTGTGACTTT  GGGCAAGCCA  1260

AGTGCCCTCT  CTGAACCTCA  GTTTCCTCAT  CTGCAAAATG  GGAACAATGA  CGTGCCTACC  1320

TCTTAGACAT  GTTGTGAGGA  GACTATGATA  TAACATGTGT  ATGTAAATCT  TCATGTGATT  1380

GTCATGTAAG  GCTTAACACA  GTGGGTGGTG  AGTTCTGACT  AAAGGTTACC  TGTTGTCGTG  1440

AAAAAAAAAA  AAAA                                                        1454
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CCGCAGATTT  AGGTGACAC                                                   19
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GGCCTCTAAT  ACGACTCAC                                                   19
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TACCACTACA  ATGGATG                                                     17
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GTTGAAGTGA  ACTTGCGGGC                                                  20
```

( 2 ) INFORMATION FOR SEQ ID NO:7:

( i ) SEQUENCE CHARACTERISTICS:
        ( A ) LENGTH: 281 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

```
Met Ser Ala Leu Leu Ile Leu Ala Leu Val Gly Ala Ala Val Ala Phe
 1               5                  10                  15
Pro Val Asp Asp Asp Lys Ile Val Gly Gly Tyr Met Met Thr Arg
            20              25                  30
Tyr Ala Arg Thr Cys Arg Glu Ser Val Pro Tyr Gln Val Ser Leu
        35              40                  45
Asn Ala Gly Tyr His Phe Cys Gly Gly Ser Leu Ile Asn Asp Gln Trp
        50              55                  60
Val Val Ser Ala Ala His Cys Tyr Lys Tyr Arg Ile Gln Val Arg Leu
 65              70                  75                  80
Gly Glu His Asn Met Met Thr Arg Tyr Ala Arg Ile Asn Val Leu Glu
                    85                  90                  95
Gly Asn Glu Gln Phe Val Asp Ser Ala Lys Ile Ile Arg His Pro Asn
                100                 105                 110
Tyr Asn Ser Trp Thr Leu Asp Asn Asp Ile Met Leu Ile Lys Leu Ala
            115                 120                 125
Ser Pro Val Thr Leu Met Met Thr Arg Tyr Ala Arg Asn Ala Arg Val
    130                 135                 140
Ala Ser Val Pro Leu Pro Ser Ser Cys Ala Pro Ala Gly Thr Gln Cys
145                 150                 155                 160
Leu Ile Ser Gly Trp Gly Asn Thr Leu Ser Asn Gly Val Asn Asn Pro
                165                 170                 175
Asp Leu Leu Gln Cys Val Asp Ala Pro Val Leu Pro Gln Ala Met Met
            180                 185                 190
Thr Arg Tyr Ala Arg Asp Cys Glu Ala Ser Tyr Pro Gly Asp Ile Thr
        195                 200                 205
Asn Asn Met Ile Cys Val Gly Phe Leu Glu Gly Gly Lys Asp Ser Cys
    210                 215                 220
Gln Gly Asp Ser Gly Gly Pro Val Val Cys Asn Gly Glu Leu Gln Gly
225                 230                 235                 240
Ile Val Ser Trp Gly Tyr Met Met Thr Arg Tyr Ala Arg Gly Cys Ala
                245                 250                 255
Gln Pro Asp Ala Pro Gly Val Tyr Thr Lys Val Cys Asn Tyr Val Asp
            260                 265                 270
Trp Ile Gln Asn Thr Ile Ala Asp Asn
        275                 280
```

( 2 ) INFORMATION FOR SEQ ID NO:8:

( i ) SEQUENCE CHARACTERISTICS:
        ( A ) LENGTH: 299 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:8:

```
Leu Glu Leu His Pro Leu Leu Gly Gly Arg Thr Trp Arg Ala Ala Arg
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Asp | Ala | Asp | Gly<br>20 | Cys | Glu | Ala | Leu | Gly<br>25 | Thr | Val | Ala | Val | Pro<br>30 | Phe | Asp |
| Asp | Asp | Asp<br>35 | Lys | Ile | Val | Gly | Gly<br>40 | Tyr | His | Ser | Thr | Arg<br>45 | Tyr | Ile | Val |
| Asx | Thr<br>50 | Cys | Glu | Asn | Ser | Leu<br>55 | Pro | Tyr | Gln | Val | Ser<br>60 | Leu | Asn | Ser | Gly |
| Ser<br>65 | His | Phe | Cys | Gly | Gly<br>70 | Ser | Leu | Ile | Ser | Glu<br>75 | Gln | Trp | Val | Val | Ser<br>80 |
| Ala | Ala | His | Cys | Tyr<br>85 | Lys | Thr | Arg | Ile | Gln<br>90 | Val | Arg | Leu | Gly | Glu<br>95 | His |
| Asn | His | Ser | Thr<br>100 | Arg | Tyr | Ile | Val | Asx<br>105 | Ile | Lys | Val | Leu | Glu<br>110 | Gly | Asn |
| Glu | Gln | Phe<br>115 | Ile | Asn | Ala | Ala | Lys<br>120 | Ile | Ile | Arg | His | Pro<br>125 | Lys | Tyr | Asn |
| Arg | Asp<br>130 | Thr | Leu | Asp | Asn | Asp<br>135 | Ile | Met | Leu | Ile | Lys<br>140 | Leu | Ser | Ser | Pro |
| Ala<br>145 | Val | Ile | His | Ser | Thr<br>150 | Arg | Tyr | Ile | Val | Asx<br>155 | Asn | Ala | Arg | Val | Ser<br>160 |
| Thr | Ile | Ser | Leu | Pro<br>165 | Thr | Ala | Pro | Ala | Ala<br>170 | Gly | Thr | Glu | Cys<br>175 | Leu |
| Ile | Ser | Gly | Trp<br>180 | Gly | Asn | Thr | Leu | Ser<br>185 | Phe | Gly | Ala | Asp | Tyr<br>190 | Pro | Asp |
| Glu | Leu | Lys<br>195 | Cys | Leu | Asp | Ala | Pro<br>200 | Val | Leu | Thr | Gln | Ala<br>205 | His | Ser | Thr |
| Arg | Tyr<br>210 | Ile | Val | Asx | Glu | Cys<br>215 | Lys | Ala | Ser | Tyr | Pro<br>220 | Gly | Lys | Ile | Thr |
| Asn<br>225 | Ser | Met | Phe | Cys | Val<br>230 | Gly | Phe | Leu | Glu | Gly<br>235 | Gly | Lys | Asp | Ser | Cys<br>240 |
| Gln | Arg | Asp | Ser | Gly<br>245 | Gly | Pro | Val | Val | Cys<br>250 | Asn | Gly | Gln | Leu | Gln<br>255 | Gly |
| Val | Val | Ser | Trp<br>260 | Gly | His | His | Ser | Thr<br>265 | Arg | Tyr | Ile | Val | Asx<br>270 | Gly | Cys |
| Ala | Trp | Lys<br>275 | Asn | Arg | Pro | Gly | Val<br>280 | Tyr | Thr | Lys | Val | Tyr<br>285 | Asn | Tyr | Val |
| Asp | Trp<br>290 | Ile | Lys | Asp | Thr | Ile<br>295 | Ala | Ala | Asn | Ser |

(2) INFORMATION FOR SEQ ID NO:9:

(i) SEQUENCE CHARACTERISTICS:
        (A) LENGTH: 286 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

|   |   |   |   |   |   |   |   |   |   |   |   |   |   |   |
|---|---|---|---|---|---|---|---|---|---|---|---|---|---|---|
| Met<br>1 | Lys | Ile | Cys | Ile<br>5 | Phe | Phe | Thr | Leu | Leu<br>10 | Gly | Thr | Val | Ala | Ala<br>15 | Phe |
| Pro | Thr | Glu | Asp<br>20 | Asn | Asp | Asp | Arg | Ile<br>25 | Val | Gly | Gly | Tyr | Arg<br>30 | Asn | Thr |
| Arg | Tyr | Pro<br>35 | Val | Asx | Thr | Cys | Gln<br>40 | Glu | His | Ser | Val | Pro<br>45 | Tyr | Gln | Val |
| Ser | Leu<br>50 | Asn | Ala | Gly | Ser | His<br>55 | Ile | Cys | Gly | Gly | Ser<br>60 | Leu | Ile | Thr | Asp |

-continued

```
Gln  Trp  Val  Leu  Ser  Ala  Ala  His  Cys  Tyr  His  Pro  Gln  Leu  Gln  Val
 65                  70                   75                            80

Arg  Leu  Gly  Glu  His  Asn  Arg  Asn  Thr  Arg  Tyr  Pro  Val  Asx  Ile  Tyr
                85                        90                            95

Glu  Ile  Glu  Gly  Ala  Glu  Gln  Phe  Ile  Asp  Ala  Ala  Lys  Met  Ile  Leu
               100                       105                      110

His  Pro  Asp  Tyr  Asp  Lys  Trp  Thr  Val  Asp  Asn  Asp  Ile  Met  Leu  Ile
          115                            120                      125

Lys  Leu  Lys  Ser  Pro  Ala  Thr  Leu  Arg  Asn  Thr  Arg  Tyr  Pro  Val  Asx
     130                      135                      140

Asn  Ser  Lys  Val  Ser  Thr  Ile  Pro  Leu  Pro  Gln  Tyr  Cys  Pro  Thr  Ala
145                      150                      155                       160

Gly  Thr  Glu  Cys  Leu  Val  Ser  Gly  Trp  Gly  Val  Leu  Lys  Phe  Gly  Phe
                    165                       170                       175

Glu  Ser  Pro  Ser  Val  Leu  Gln  Cys  Leu  Asp  Ala  Pro  Val  Leu  Ser  Asp
               180                       185                      190

Ser  Arg  Asn  Thr  Arg  Tyr  Pro  Val  Asx  Val  Cys  His  Lys  Ala  Tyr  Pro
          195                       200                      205

Arg  Gln  Ile  Thr  Asn  Asn  Met  Phe  Cys  Leu  Gly  Phe  Leu  Glu  Gly  Gly
     210                      215                      220

Lys  Asp  Ser  Cys  Gln  Tyr  Asp  Ser  Gly  Gly  Pro  Val  Val  Cys  Asn  Gly
225                            230                      235                 240

Glu  Val  Gln  Gly  Ile  Val  Ser  Trp  Gly  Asp  Arg  Asn  Thr  Arg  Tyr  Pro
                    245                       250                      255

Val  Asx  Gly  Cys  Ala  Leu  Glu  Gly  Lys  Pro  Gly  Val  Tyr  Thr  Lys  Val
               260                       265                      270

Cys  Asn  Tyr  Leu  Asn  Trp  Ile  Gln  Gln  Thr  Val  Ala  Ala  Asn
          275                       280                 285
```

( 2 ) INFORMATION FOR SEQ ID NO:10:

( i ) SEQUENCE CHARACTERISTICS:
       ( A ) LENGTH: 271 amino acids
       ( B ) TYPE: amino acid
       ( C ) STRANDEDNESS: Not Relevant
       ( D ) TOPOLOGY: linear ( i i ) MOLECULE TYPE: protein ( x i ) SEQUENCE DESCRIPTION: SEQ ID NO:10:

```
Ala  Ala  Phe  Ala  Thr  Glu  Asp  Asp  Lys  Ile  Val  Gly  Gly  Tyr  Ser  Ser
 1                   5                   10                           15

Thr  Arg  Tyr  Pro  Ile  Ile  Glu  Cys  Lys  Ala  Tyr  Ser  Gln  Pro  His  Gln
               20                        25                      30

Val  Ser  Leu  Asn  Ser  Gly  Tyr  His  Phe  Cys  Gly  Gly  Ser  Leu  Val  Asn
                35                        40                      45

Glu  Asn  Trp  Val  Val  Ser  Ala  Ala  His  Cys  Tyr  Gln  Ser  Arg  Val  Glu
           50                        55                 60

Val  Arg  Leu  Gly  Glu  His  Asn  Ser  Ser  Thr  Arg  Tyr  Pro  Ile  Ile  Ile
 65                      70                        75                      80

Gln  Val  Thr  Glu  Gly  Ser  Glu  Gln  Phe  Ile  Ser  Ser  Ser  Arg  Val  Ile
                    85                        90                      95

Arg  His  Pro  Asn  Tyr  Ser  Ser  Tyr  Asn  Ile  Asp  Asn  Asp  Ile  Met  Leu
               100                       105                      110

Ile  Lys  Leu  Ser  Lys  Pro  Ala  Thr  Leu  Ser  Ser  Thr  Arg  Tyr  Pro  Ile
          115                       120                      125
```

```
Ile  Asn  Thr  Tyr  Val  Gln  Pro  Val  Ala  Leu  Pro  Thr  Ser  Cys  Ala  Pro
     130                 135                 140

Ala  Gly  Thr  Met  Cys  Thr  Val  Ser  Gly  Trp  Gly  Asn  Thr  Met  Ser  Ser
145                      150                 155                           160

Thr  Ala  Asp  Lys  Asn  Lys  Leu  Gln  Cys  Leu  Asn  Ile  Pro  Ile  Leu  Ser
               165                      170                      175

Tyr  Ser  Ser  Ser  Thr  Arg  Tyr  Pro  Ile  Ile  Asp  Cys  Asn  Asn  Ser  Tyr
               180                      185                      190

Pro  Gly  Met  Ile  Thr  Asn  Ala  Met  Phe  Cys  Ala  Gly  Tyr  Leu  Glu  Gly
          195                      200                      205

Gly  Lys  Asp  Ser  Cys  Gln  Gly  Asp  Ser  Gly  Gly  Pro  Val  Val  Cys  Asn
     210                      215                      220

Gly  Glu  Leu  Gln  Gly  Val  Val  Ser  Trp  Gly  Tyr  Ser  Ser  Thr  Arg  Tyr
225                           230                 235                      240

Pro  Ile  Ile  Gly  Cys  Ala  Glu  Pro  Gly  Asn  Pro  Gly  Val  Tyr  Ala  Lys
               245                      250                      255

Val  Cys  Ile  Phe  Asn  Asp  Trp  Leu  Thr  Ser  Thr  Met  Ala  Thr  Tyr
               260                 265                      270
```

( 2 ) INFORMATION FOR SEQ ID NO:11:

( i ) SEQUENCE CHARACTERISTICS:
        ( A ) LENGTH: 291 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:11:

```
Met  Arg  Ala  Pro  His  Leu  His  Leu  Ser  Ala  Ala  Ser  Gly  Ala  Arg  Ala
1                   5                   10                      15

Leu  Ala  Lys  Leu  Leu  Pro  Leu  Leu  Met  Ala  Gln  Leu  Trp  Ala  Ala  Glu
               20                      25                      30

Ala  Ala  Leu  Leu  Pro  Gln  Asn  Asp  Thr  Arg  Leu  Asp  Pro  Glu  Ala  Tyr
               35                      40                      45

Gly  Ala  Asn  Glu  Ser  Pro  Cys  Ala  Arg  Gly  Ser  Gln  Pro  Trp  Gln  Val
     50                      55                      60

Ser  Leu  Phe  Asn  Gly  Leu  Ser  Phe  His  Cys  Ala  Gly  Val  Leu  Val  Asp
65                       70                      75                           80

Gln  Ser  Trp  Val  Leu  Thr  Ala  Ala  His  Cys  Gly  Asn  Lys  Pro  Leu  Trp
                    85                      90                      95

Ala  Arg  Val  Gly  Asp  Asp  His  Asn  Glu  Ser  Leu  Leu  Leu  Leu  Gln  Gly
                    100                     105                     110

Glu  Gln  Leu  Arg  Arg  Thr  Thr  Arg  Ser  Val  Val  His  Pro  Lys  Tyr  His
               115                     120                     125

Gln  Gly  Ser  Gly  Pro  Ile  Leu  Pro  Arg  Arg  Thr  Asp  Glu  His  Asp  Leu
     130                     135                     140

Met  Leu  Leu  Lys  Leu  Ala  Arg  Pro  Val  Val  Pro  Asn  Glu  Ser  Gly  Pro
145                     150                     155                          160

Arg  Val  Arg  Ala  Leu  Gln  Leu  Pro  Tyr  Arg  Cys  Ala  Gln  Pro  Gly  Asp
                    165                     170                     175

Gln  Cys  Gln  Val  Ala  Gly  Trp  Gly  Thr  Thr  Ala  Ala  Arg  Arg  Val  Lys
               180                     185                     190

Tyr  Asn  Lys  Gly  Leu  Thr  Cys  Ser  Ser  Ile  Thr  Ile  Leu  Ser  Pro  Lys
          195                     200                     205

Asn  Glu  Ser  Glu  Cys  Glu  Val  Phe  Tyr  Pro  Gly  Val  Val  Thr  Asn  Asn
```

-continued

|  |  |  |  |  | 210 |  |  |  | 215 |  |  |  | 220 |  |  |
|---|---|---|---|---|---|---|---|---|---|---|---|---|---|---|---|
| Met 225 | Ile | Cys | Ala | Gly | Leu 230 | Asp | Arg | Gly | Gln | Asp 235 | Pro | Cys | Gln | Ser | Asp 240 |
| Ser | Gly | Gly | Pro | Leu 245 | Val | Cys | Asp | Glu | Thr 250 | Leu | Gln | Gly | Ile | Leu 255 | Ser |
| Trp | Gly | Val | Tyr 260 | Asn | Glu | Ser | Pro | Cys 265 | Gly | Ser | Ala | Gln | His 270 | Pro | Ala |
| Val | Tyr | Thr 275 | Gln | Ile | Cys | Lys | Tyr 280 | Met | Ser | Trp | Ile | Asn 285 | Lys | Val | Ile |
| Arg | Ser | Asn 290 |  |  |  |  |  |  |  |  |  |  |  |  |  |